US012781244B2

(12) United States Patent
Shi et al.

(10) Patent No.: US 12,781,244 B2
(45) Date of Patent: Nov. 3, 2026

(54) COMPOSITION AND METHOD FOR TREATING EYE DISEASES

(71) Applicant: FTGEN Corp, Watertown, MA (US)

(72) Inventors: Zhongdong Shi, Bedford, MA (US); Wei Zhao, Boston, MA (US)

(73) Assignee: FTGEN Corp, Watertown, MA (US)

(*) Notice: Subject to any disclaimer, the term of this patent is extended or adjusted under 35 U.S.C. 154(b) by 852 days.

(21) Appl. No.: 18/157,599

(22) Filed: Jan. 20, 2023

(65) Prior Publication Data

US 2023/0295243 A1 Sep. 21, 2023

Related U.S. Application Data

(63) Continuation of application No. PCT/IB2021/000498, filed on Jul. 20, 2021.

(30) Foreign Application Priority Data

Jul. 21, 2020 (CN) ........................ 202010706505.5
Jul. 21, 2020 (CN) ........................ 202010706658.X

(51) Int. Cl.

| | |
|---|---|
| ***C07K 14/075*** | (2006.01) |
| ***A61K 48/00*** | (2006.01) |
| ***A61P 27/02*** | (2006.01) |
| ***C07K 14/47*** | (2006.01) |
| ***C12N 15/86*** | (2006.01) |

(52) U.S. Cl.

CPC ............ *C12N 15/86* (2013.01); *A61K 48/005* (2013.01); *A61P 27/02* (2018.01); *C07K 14/075* (2013.01); *C07K 14/4703* (2013.01); *C12N 2750/14143* (2013.01)

(58) Field of Classification Search

CPC .......... C12N 15/86; C12N 2750/14143; A61K 48/005; A61P 27/02; C07K 14/075; C07K 14/4703; C07K 2319/30; C07K 14/71

See application file for complete search history.

(56) References Cited

U.S. PATENT DOCUMENTS

| | | | |
|---|---|---|---|
| 5,786,464 A | 7/1998 | Seed | |
| 6,114,148 A | 9/2000 | Seed et al. | |
| 2011/0033429 A1 | 2/2011 | Notka et al. | |
| 2015/0104832 A1 | 4/2015 | Notka et al. | |
| 2020/0282077 A1* | 9/2020 | Kirn .................. | A61K 48/0008 |

FOREIGN PATENT DOCUMENTS

| | | | |
|---|---|---|---|
| CN | 101035899 | A | 9/2007 |
| CN | 105026433 | A | 11/2015 |
| CN | 108347932 | A | 7/2018 |
| CN | 109641065 | A | 4/2019 |
| EP | 4349852 | A1 | 4/2024 |
| JP | 2008507986 | A | 3/2008 |
| JP | 2021500071 | A | 1/2021 |
| JP | 2021503914 | A | 2/2021 |
| JP | 2021506861 | A | 2/2021 |
| WO | WO-2016134375 | A1 | 8/2016 |
| WO | WO-2017218974 | A2 | 12/2017 |
| WO | WO-2019079494 | A1 | 4/2019 |
| WO | WO-2019104279 | A1 | 5/2019 |
| WO | WO-2019126329 | A1 | 6/2019 |
| WO | WO-2019195423 | A1 | 10/2019 |
| WO | WO-2020102645 | A1 | 5/2020 |
| WO | WO-2021050649 | A1 | 3/2021 |
| WO | WO-2022018516 | A1 | 1/2022 |
| WO | WO-2022079453 | A1 | 4/2022 |
| WO | WO-2022217110 | A1 | 10/2022 |
| WO | WO-2022232178 | A1 | 11/2022 |

OTHER PUBLICATIONS

Aponte-Ubillus et al. 2018. Molecular design for recombinant adeno-associated virus (rAAV) vector production. Applied microbiology and biotechnology, 102(3), 1045-1054. (Year: 2018).*

Rudikoff et al. 1982. Single amino acid substitution altering antigen-binding specificity. Proceedings of the National Academy of Sciences, 79(6), 1979-1983. (Year: 1982).*

Panka et al. 1988. Variable region framework differences result in decreased or increased affinity of variant anti-digoxin antibodies. Proceedings of the National Academy of Sciences, 85(9), 3080-3084. (Year: 1988).*

Muller et al. 1998. VEGF and the Fab fragment of a humanized neutralizing antibody: crystal structure of the complex at 2.4 Å resolution and mutational analysis of the interface. Structure, 6(9), 1153-1167. (Year: 1998).*

Scheule, R. K. 2000. The role of CpG motifs in immunostimulation and gene therapy. Advanced drug delivery reviews, 44(2-3), 119-134. (Year: 2000).*

EP21845723.2 Extended Supplementary European Search Report dated Aug. 5, 2024.

Grishanin; R. et al.: Preclinical Evaluation of ADVM-022, a Novel Gene Therapy Approach to Treating Wet Age-Related Macular Degeneration. Molecular Therapy 27(1):118-129 (2019).

Alfthan et al. Properties of a single-chain antibody containing different linker peptides. Protein Eng. 8:725-731 (1995).

Bird et al. Single-chain antigen-binding proteins. Science 242(4877):423-426 (1988).

Choi et al. Recombinant chimeric OKT3 scFv IgM antibodies mediate immune suppression while reducing T cell activation in vitro. Eur. J Immunol. 31:94-106 (2001).

Chothia et al. Canonical structures for the hypervariable regions of immunoglobulins. J Mol Biol 196:901-917 (1987).

Chothia et al. Conformations of immunoglobulin hypervariable regions. Nature 342:878-883 (1989).

(Continued)

*Primary Examiner* — Arthur S Leonard
*Assistant Examiner* — Erin V Paulus
(74) *Attorney, Agent, or Firm* — Wilson Sonsini Goodrich & Rosati

(57) ABSTRACT

The present invention relates to a system for treating eye diseases, and a method for treating eye diseases using the system.

11 Claims, 2 Drawing Sheets

Specification includes a Sequence Listing.

(56) References Cited

OTHER PUBLICATIONS

Chu et al. SV40 DNA transfection of cells in suspension: analysis of efficiency of transcription and translation of T-antigen. Gene 13:197-202 (1981).
Graham et al. A new technique for the assay of infectivity of human adenovirus 5 DNA. Virology 52:456-467 (1973).
Holliger et al. "Diabodies": small bivalent and bispecific antibody fragments. PNAS USA 90(14):6444-6448 (1993).
Hu et al., Minibody: A novel engineered anti-carcinoembryonic antigen antibody fragment (single-chain Fv-CH3) which exhibits rapid, high-level targeting of xenografts. Cancer Res. 56(13):3055-3061 (1996).
Huston et al. Protein engineering of antibody binding sites: recovery of specific activity in an anti-digoxin single-chain Fv analogue produced in *Escherichia coli*. PNAS USA 85(16):5879-5883 (1988).
Kabat et al. Sequences of proteins of immunological interest. NIH Publ. No. 91-3242 1:647-669 (1991).
Kipriyanov et al. Bispecific tandem diabody for tumor therapy with improved antigen binding and pharmacokinetics. J Mol Biol 293:41-56 (1999).
Kumar et al. Cloning vector pRNBZMB, complete sequence, GenBank: MH507507.1 NCBI, Apr. 10, 2019.
Leppanen et al. Chain L, Vascular Endothelial Growth Factor Receptor 2, PDB: 2X1W_L NCBI, Oct. 10, 2012.
PCT/IB2021/000498 International Search Report and Written Opinion dated Dec. 30, 2021.
Roovers et al. In vitro characterisation of a monovalent and bivalent form of a fully human anti Ep-CAM phage antibody. Cancer Immunol. 50(1):51-59 (2001).
Smith et al. Production of human beta interferon in insect cells infected with a baculovirus expression vector. Mol Cell Biol. 3(12):2156-2165 (1983).
Wang et al. Adeno-associated virus serotype 8 efficiently delivers genes to muscle and heart. Nat Biotech 23:321-328 (2005).
Alfthan, Kaija et al.: Properties of a single-chain antibody containing different linker peptides. Protein Engineering 8(7):725-731 (1995). https://doi.org/10.1093/protein/8.7.725 (Abstract).
Bird, Robert E. et al.: Single-Chain Antigen-Binding Proteins. Science 242(4877):423-426 (1988). DOI: 10.1126/science.3140379.
Choi, Joo Young et al.: Aberrant CFTR-dependent HCA3 transport in mutations associated with cystic fibrosis. Nature 410(6824):94-97 (2001). doi:10.1038/35065099.
Chothia, Cyrus et al: Canonical structures for the hypervariable regions of immunoglobulins. Journal of Molecular Biology 196(4):901-917 (1987). https://doi.org/10.1016/0022-2836(87)90412-8.
Chothia, Cyrus et al.: Conformations of immunoglobulin hypervariable regions. Nature 342(6252):877-883 (1989). DOI:10.1038/342877a0.
Green, Michael R. et al.: Molecular Cloning: A Laboratory Manual, 4th Edition (2012).
Harlow; Ed: Antibodies: A Laboratory Manual. Cold Spring Harbor Laboratory (1988).
Holliger, P. et al.: "Diabodies": small bivalent and bispecific antibody fragments. PNAS 90(14):6444-6448 (1993). https://doi.org/10.1073/pnas.90.14.6444.
Huston, J.S. et al.: Protein engineering of antibody binding sites: recovery of specific activity in an anti-digoxin single-chain Fv analogue produced in *Escherichia coli*. PNAS 85(16):5879-5883 (1988). https://doi.org/10.1073/pnas.85.16.5879.
Ozawa, Takaya: Gene therapy using AAV. Uirusu, Jun. 1, 2007, 57(1):47-55, (English Abstract), https://doi.org/10.2222/jsv.57.47.
Ozawa, Keiya: Gene therapy using AAV. Uirusu. 57(1):47-55 (2007). doi: 10.2222/jsv.57.47.

* cited by examiner

SEQUENCE LISTING

```
Sequence total quantity: 20
SEQ ID NO: 1            moltype = AA  length = 431
FEATURE                 Location/Qualifiers
source                  1..431
                        mol_type = protein
                        organism = Homo sapiens
SEQUENCE: 1
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP G                                                      431

SEQ ID NO: 2            moltype = AA  length = 210
FEATURE                 Location/Qualifiers
source                  1..210
                        mol_type = protein
                        organism = Homo sapiens
SEQUENCE: 2
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEDPIEGR                                  210

SEQ ID NO: 3            moltype = AA  length = 103
FEATURE                 Location/Qualifiers
source                  1..103
                        mol_type = protein
                        organism = Homo sapiens
SEQUENCE: 3
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IID                   103

SEQ ID NO: 4            moltype = AA  length = 107
FEATURE                 Location/Qualifiers
source                  1..107
                        mol_type = protein
                        organism = Homo sapiens
SEQUENCE: 4
VVLSPSHGIE LSVGEKLVLN CTARTELNVG IDFNWEYPSS KHQHKKLVNR DLKTQSGSEM  60
KKFLSTLTID GVTRSDQGLY TCAASSGLMT KKNSTFVRVH EDPIEGR               107

SEQ ID NO: 5            moltype = AA  length = 10
FEATURE                 Location/Qualifiers
source                  1..10
                        mol_type = protein
                        organism = Homo sapiens
SEQUENCE: 5
GYDFTHYGMN                                                        10

SEQ ID NO: 6            moltype = AA  length = 17
FEATURE                 Location/Qualifiers
source                  1..17
                        mol_type = protein
                        organism = Homo sapiens
SEQUENCE: 6
WINTYTGEPT YAADFKR                                                17

SEQ ID NO: 7            moltype = AA  length = 14
```

-continued

```
FEATURE                 Location/Qualifiers
source                  1..14
                        mol_type = protein
                        organism = Homo sapiens
SEQUENCE: 7
YPYYYGTSHW YFDV                                                 14

SEQ ID NO: 8            moltype = AA  length = 11
FEATURE                 Location/Qualifiers
source                  1..11
                        mol_type = protein
                        organism = Homo sapiens
SEQUENCE: 8
SASQDISNYL N                                                    11

SEQ ID NO: 9            moltype = AA  length = 7
FEATURE                 Location/Qualifiers
source                  1..7
                        mol_type = protein
                        organism = Homo sapiens
SEQUENCE: 9
FTSSLHS                                                         7

SEQ ID NO: 10           moltype = AA  length = 9
FEATURE                 Location/Qualifiers
source                  1..9
                        mol_type = protein
                        organism = Homo sapiens
SEQUENCE: 10
QQYSTVPWT                                                       9

SEQ ID NO: 11           moltype = AA  length = 231
FEATURE                 Location/Qualifiers
source                  1..231
                        mol_type = protein
                        organism = Homo sapiens
SEQUENCE: 11
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH L           231

SEQ ID NO: 12           moltype = AA  length = 214
FEATURE                 Location/Qualifiers
source                  1..214
                        mol_type = protein
                        organism = Homo sapiens
SEQUENCE: 12
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 13           moltype = DNA  length = 1377
FEATURE                 Location/Qualifiers
source                  1..1377
                        mol_type = other DNA
                        organism = Homo sapiens
SEQUENCE: 13
atggtcagct actgggacac cggggtcctg ctgtgcgcgc tgctcagctg tctgcttctc  60
acaggatcta gttccggaag tgataccggt agacctttcg tagagatgta cagtgaaatc  120
cccgaaatta tacacatgac tgaaggaagg gagctcgtca ttccctgccg ggttacgtca  180
cctaacatca ctgttacttt aaaaaagttt ccacttgaca ctttgatccc tgatggaaaa  240
cgcataatct gggacagtag aaagggcttc atcatatcaa atgcaacgta caaagaaata  300
gggcttctga cctgtgaagc aacagtcaat gggcatttgt ataagacaaa ctatctcaca  360
catcgacaaa ccaatacaat catagatgtg gttctgagtc cgtctcatgg aattgaacta  420
tctgttggag aaaagcttgt cttaaattgt acagcaagaa ctgaactaaa tgtggggatt  480
gacttcaact gggaataccc ttcttcgaag catcagcata agaaacttgt aaaccgagac  540
ctaaaaaccc agtctgggag tgagatgaag aaatttttga gcaccttaac tatagatggt  600
gtaacccgga gtgaccaagg attgtacacc tgtgcagcat ccagtgggct gatgaccaag  660
aagaacagca catttgtcag ggtccatgaa aaggacaaaa ctcacacatg cccaccgtgc  720
ccagcacctg aactcctggg gggaccgtca gtcttcctct tccccccaaa acccaaggac  780
accctcatga tctcccggac ccctgaggtc acatgcgtgg tggtggacgt gagccacgaa  840
gaccctgagg tcaagttcaa ctggtacgtg gacggcgtgg aggtgcataa tgccaagaca  900
aagccgcggg aggagcagta caacagcacg taccgtgtgg tcagcgtcct caccgtcctg  960
caccaggact ggctgaatgg caaggagtac aagtgcaagg tctccaacaa agccctccca  1020
gcccccatcg agaaaaccat ctccaaagcc aaagggcagc cccgagaacc acaggtgtac  1080
accctgcccc catcccggga tgagctgacc aagaaccagg tcagcctgac ctgcctggtc  1140
aaaggcttct atcccagcga catcgccgtg gagtgggaga gcaatgggca gccggagaac  1200
```

```
aactacaaga ccacgcctcc cgtgctggac tccgacggct ccttcttcct ctacagcaag  1260
ctcaccgtgg acaagagcag gtggcagcag gggaacgtct tctcatgctc cgtgatgcat  1320
gaggctctgc acaaccacta cacgcagaag agcctctccc tgtctccggg taaatga     1377

SEQ ID NO: 14          moltype = DNA  length = 1377
FEATURE                Location/Qualifiers
source                 1..1377
                       mol_type = other DNA
                       organism = Homo sapiens
SEQUENCE: 14
atggtttctt actgggatac cggcgtgctg ctgtgtgccc tgctgtcttg tctgctgctg  60
accggctcta gcagcggctc tgataccggc agacccttcg tggaaatgta cagcgagatc  120
cccgagatca tccacatgac cgagggcaga gagctggtca tcccctgcag agtgacaagc  180
cccaacatca ccgtgactct gaagaagttc cctctggaca cactgatccc cgacggcaag  240
agaatcatct gggacagccg gaagggcttc atcatcagca acgccaccta caaagagatc  300
ggcctgctga cctgtgaagc caccgtgaat ggccacctgt acaagaccaa ctacctgaca  360
cacagacaga ccaacaccat catcgacgtg gtgctgagcc ctagccacgg cattgaactg  420
tctgtgggcg agaagctggt gctgaactgt accgccagaa ccgagctgaa cgtgggcatc  480
gacttcaact gggagtaccc cagcagcaag caccagcaca agaaactggt caaccgggac  540
ctgaaaaccc agagcggcag cgagatgaag aaattcctga gcaccctgac catcgacggc  600
gtgaccaggt ctgaccaggg cctgtacaca tgtgccgcca gctctggcct gatgaccaag  660
aaaaacagca ccttcgtgcg ggtgcacgag aaggacaaga cccacacctg tcctccatgt  720
cctgctccag aactgctcgg cggaccttcc gtgttcctgt tcctccaaa gcctaaggac   780
accctgatga tcagcagaac ccctgaagtg acctgcgtgg tggtggatgt gtcccacgag  840
gatcccgaag tgaagttcaa ctggtacgtg gacggcgtgg aagtgcacaa cgccaagacc  900
aagcctagag aggaacagta caatagcacc tacagagtgg tgtccgtgct gaccgtgctg  960
caccaggatt ggctgaacgg caaagagtac aagtgcaagg tgtccaacaa ggccctgcct  1020
gctcctatcg agaaaaccat ctccaaggcc aagggccagc ccagggaacc ccaggtttac  1080
acactgcctc caagcaggga cgagctgaca aagaaccagg tgtccctgac ctgcctggtc  1140
aagggcttct acccttccga tatcgccgtg gaatgggaga gcaatggcca gcctgagaac  1200
aactacaaga caacccctcc tgtgctggac agcgacggct cattcttcct gtacagcaag  1260
ctgacagtgg acaagagcag atggcagcag ggaaacgtgt tcagctgcag cgtgatgcac  1320
gaggccctgc acaaccacta cacccagaag tccctgagcc tgtctcctgg caagtga     1377

SEQ ID NO: 15          moltype = DNA  length = 1377
FEATURE                Location/Qualifiers
source                 1..1377
                       mol_type = other DNA
                       organism = Homo sapiens
SEQUENCE: 15
atggtcagct attgggatac gggcgtcctc ctttgtgccc ttctgagttg tctcttgttg  60
acgggaagta gttccggaag tgacactggc cgaccatttg tagaaatgta cagtgagatc  120
ccggaaatca tccacatgac cgaaggccgg gagttggtta taccatgccg ggtgacatcc  180
ccgaacatta ccgttacact gaagaaattc ccattggaca ctttgatacc tgatggaaag  240
agaatcatct gggattccag aaaaggcttt attatctcaa atgctacata caaagaaatc  300
ggtcttctta cgtgtgaagc aaccgtgaat ggtcatttgt acaagactaa ctacctcacc  360
cacaggcaga ccaatacaat aatcgacgtc gttctcagcc cctcccacgg aattgagctt  420
agtgtggggg agaaattggt cttgaattgt accgcccgga cagagttgaa tgttggcatt  480
gacttcaatt gggagtatcc atctagtaag caccaacaca aaaagcttgt taatcgggac  540
ctgaagactc aaagcggatc agaaatgaaa aagtttctct caacgttgac aatagacggc  600
gtgacgcgct ctgatcaggg tctttacacc tgcgctgcca gctctgggtt gatgacgaaa  660
aaaaattcta catttgtgcg ggttcatgaa aaagataaga cacatacctg tcccccgtgt  720
ccagcgccgg aattgcttgg gggccccagc gtattccttt tcccccccaa gcctaaagac  780
acgctcatga tctctagaac gccggaggtc acctgtgtgg tggtggacgt gtctcatgaa  840
gatcccgagg ttaaattcaa ttggtacgta gatggagtcg aagttcacaa tgcaaagaca  900
aagccgagag aagagcagta caatagcacc taccgagttg taagtgtact tactgtcctg  960
caccaagatt ggttgaatgg aaaagagtat aagtgtaagg tctcaaataa ggcactccca  1020
gctcccatag aaaaaacgat atctaaagcg aagggtcagc ccagagagcc tcaagtgtac  1080
acgctccctc cctcacggga tgagctgaca aaaaaccagg tttcactgac ttgtttggta  1140
aagggttttt atccatctga catcgctgtc gagtgggaaa gcaatggtca accggagaac  1200
aactataaga caacccccccc ggttctcgat tcagatggct ccttcttcct ctattctaag  1260
ctcactgttg ataaatctcg gtggcaacaa gggaatgttt tctcttgctc tgttatgcac  1320
gaagcattgc ataatcatta tacacaaaaa tctctttccc ttagtccagg taaatga     1377

SEQ ID NO: 16          moltype = DNA  length = 1377
FEATURE                Location/Qualifiers
source                 1..1377
                       mol_type = other DNA
                       organism = Homo sapiens
SEQUENCE: 16
atggtgtcct actgggacac aggggtgctg ctgtgtgccc tgctgtcttg tctgctgctg  60
actggctcta gctctggctc tgacacaggc agaccctttg tggaaatgta ctctgagatc  120
cctgagatca tccacatgac agagggcaga gagctggtca tcccctgcag agtgacaagc  180
cccaacatca cagtgaccct gaagaagttc cctctggaca cactgatccc tgatggcaag  240
agaatcatct gggacagcag aaagggcttc atcatcagca atgccaccta caaagagatt  300
ggcctgctga cctgtgaagc cacagtgaat ggccacctgt acaagaccaa ctacctgaca  360
cacagacaga ccaacaccat cattgatgtg gtgctgagcc ccagccatgg cattgagctg  420
tctgtgggag agaagctggt gctgaactgc acagccagaa cagagctgaa tgtgggcatt  480
gacttcaact gggagtaccc cagcagcaag caccagcaca agaaactggt caacagggac  540
```

```
ctgaaaaccc agagtggctc tgagatgaag aaattcctga gcaccctgac cattgatggg  600
gtcaccagat ctgaccaggg cctgtacaca tgtgctgcca gctctggact gatgaccaag  660
aaaaacagca cctttgtcag agtgcatgag aaggacaaga cccacacctg tcctccatgt  720
cctgcacctg agctgcttgg aggcccctct gtgttcctgt ttcctccaaa gcctaaggac  780
accctgatga tcagcagaac acctgaagtg acctgtgtgg tggtggatgt gtcccatgag  840
gacccagaag tgaagttcaa ttggtatgtg gatggggttg aagtgcacaa tgccaagacc  900
aagcctagag aggaacagta caactccacc tacagagtgg tgtcagtgct gacagtgctg  960
caccaggact ggctgaatgg caaagagtac aagtgcaagg tgtccaacaa ggccctgcct  1020
gctcctattg agaaaaccat ctccaaggcc aagggccagc ctagggaacc ccaggtttac  1080
acactgccac ctagcaggga tgagctgaca aagaaccagg tgtccctgac ctgcctggtc  1140
aagggcttct accccctctga cattgctgtg gaatgggaga gcaatggcca gcctgagaac  1200
aactacaaga caacccctcc tgtgctggac tctgatggct cattcttcct gtacagcaag  1260
ctgactgtgg acaagagcag atggcagcag ggaaatgtgt tcagctgctc tgtgatgcat  1320
gaggccctgc acaaccacta cacccagaaa agcctgagcc tgtctcctgg caagtga     1377

SEQ ID NO: 17          moltype = DNA  length = 1377
FEATURE                Location/Qualifiers
source                 1..1377
                       mol_type = other DNA
                       organism = Homo sapiens
SEQUENCE: 17
atggtttctt actgggatac cggcgtgctg ctgtgtgccc tgctgtcttg tctgctgctg  60
accggctcta gcagcggctc tgataccggc agacccttcg tggaaatgta cagcgagatc  120
cccgagatca tccacatgac cgagggcaga gagctggtca tcccctgcag agtgacaagc  180
cccaacatca ccgtgactct gaagaagttc cctctggaca cactgatccc cgacggcaag  240
agaatcatct gggacagccg gaagggcttc atcatcagca acgccaccta caaagagatc  300
ggcctgctga cctgtgaagc caccgtgaat ggccacctgt acaagaccaa ctacctgaca  360
cacagacaga ccaacaccat catcgacgtg gtgctgagcc ctagccacgg cattgaactg  420
tctgtgggcg agaagctggt gctgaactgt accgccagaa ccgagctgaa cgtgggcatc  480
gacttcaact gggagtaccc cagcagcaag caccagcaca agaaactggt caaccgggac  540
ctgaaaaccc agagcggcag cgagatgaag aaattcctga gcaccctgac catcgacggc  600
gtgaccaggt ctgaccaggg cctgtacaca tgtgccgcca gctctggcct gatgaccaag  660
aaaaacagca ccttcgtgcg ggtgcacgag aaggacaaga cccacacctg tcctccatgt  720
cctgctccag aactgctcgg cggaccttcc gtgttcctgt ttcctccaaa gcctaaggac  780
accctgatga tcagcagaac ccctgaagtg acctgcgtgg tggtggatgt gtcccacgag  840
gatcccgaag tgaagttcaa ctggtacgtg gacggcgtgg aagtgcacaa cgccaagacc  900
aagcctagag aggaacagta caatagcacc tacagagtgg tgtccgtgct gaccgtgctg  960
caccaggatt ggctgaacgg caaagagtac aagtgcaagg tgtccaacaa ggccctgcct  1020
gctcctatcg agaaaaccat ctccaaggcc aagggccagc ccagggaacc ccaggtttac  1080
acactgcctc caagcaggga cgagctgaca aagaaccagg tgtccctgac ctgcctggtc  1140
aagggcttct acccttccga tatcgccgtg gaatgggaga gcaatggcca gcctgagaac  1200
aactacaaga caacccctcc tgtgctggac agcgacggct cattcttcct gtacagcaag  1260
ctgacagtgg acaagagcag atggcagcag ggaaacgtgt tcagctgcag cgtgatgcac  1320
gaggccctgc acaaccacta cacccagaag tccctgagcc tgtctcctgg caagtga     1377

SEQ ID NO: 18          moltype = DNA  length = 1377
FEATURE                Location/Qualifiers
source                 1..1377
                       mol_type = other DNA
                       organism = Homo sapiens
SEQUENCE: 18
atggtgtcct actgggatac aggcgtgctg ctgtgtgccc tgctgtcttg tctgctgctg  60
accggctcta gcagcggctc tgataccggc agacccttcg tggaaatgta cagcgagatc  120
cccgagatca tccacatgac cgagggcaga gagctggtca tcccctgcag agtgacaagc  180
cccaacatca ccgtgactct gaagaagttc cctctggaca cactgatccc cgacggcaag  240
agaatcatct gggacagccg gaagggcttc atcatcagca acgccaccta caaagagatc  300
ggcctgctga cctgtgaagc caccgtgaat ggccacctgt acaagaccaa ctacctgaca  360
cacagacaga ccaacaccat catcgacgtg gtgctgagcc ctagccacgg cattgaactg  420
tctgtgggcg agaagctggt gctgaactgt accgccagaa ccgagctgaa cgtgggcatc  480
gacttcaact gggagtaccc cagcagcaag caccagcaca agaaactggt caaccgggac  540
ctgaaaaccc agagcggcag cgagatgaag aaattcctga gcaccctgac catcgacggc  600
gtgaccagat ctgaccaggg cctgtacaca tgtgccgcca gctctggcct gatgaccaag  660
aaaaacagca ccttcgtgcg ggtgcacgag aaggacaaga cccacacctg tcctccatgt  720
cctgctccag aactgctcgg cggaccttcc gtgttcctgt ttcctccaaa gcctaaggac  780
accctgatga tcagcagaac ccctgaagtg acctgcgtgg tggtggatgt gtcccacgag  840
gatcccgaag tgaagttcaa ttggtacgtg gacggcgtgg aagtgcacaa cgccaagacc  900
aagcctagag aggaacagta caatagcacc tacagagtgg tgtccgtgct gaccgtgctg  960
caccaggatt ggctgaacgg caaagagtac aagtgcaagg tgtccaacaa ggccctgcct  1020
gctcctatcg agaaaaccat ctccaaggcc aagggccagc ctagggaacc ccaggtttac  1080
acactgcctc caagcaggga cgagctgaca aagaaccagg tgtccctgac ctgcctggtc  1140
aagggcttct acccttccga tatcgccgtg gaatgggaga gcaatggcca gcctgagaac  1200
aactacaaga caacccctcc tgtgctggac agcgacggct cattcttcct gtacagcaag  1260
ctgacagtgg acaagagcag atggcagcag ggaaacgtgt tcagctgcag cgtgatgcac  1320
gaggccctgc acaaccacta cacccagaag tccctgagcc tgtctcctgg caagtga     1377

SEQ ID NO: 19          moltype = AA  length = 5
FEATURE                Location/Qualifiers
REGION                 1..5
                       note = Description of Artificial Sequence: Synthetic peptide
```

-continued

```
source                  1..5
                        mol_type = protein
                        organism = synthetic construct
SEQUENCE: 19
GGGGS                                                                   5

SEQ ID NO: 20           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 20
GGGGSGGGGS GGGGSGGGGS                                                    20
```

COMPOSITION AND METHOD FOR TREATING EYE DISEASES

CROSS-REFERENCE TO RELATED APPLICATIONS

This application is a continuation of International Application No. PCT/IB2021/000498, filed Jul. 20, 2021, which claims the benefit of Chinese Patent Application No. 202010706658.X, filed Jul. 21, 2020 and Chinese Patent Application No. 202010706505.5, filed Jul. 21, 2020, each of which is incorporated herein by reference.

SEQUENCE LISTING

The instant application contains a Sequence Listing which has been submitted electronically in XML format and is hereby incorporated by reference in its entirety, Said copy. created on Jan. 20, 2023, is named 57837-712301_SL.xml and is 28,541 bytes in size.

BACKGROUND

Angiogenesis refers to the new formation or growth of blood vessels in tissues, or the further formation or growth of existing capillaries or blood vessels, which plays an important role in disease and health. Pathological ocular angiogenesis or neovascularization can occur in the retina, choroid and cornea and can cause severe visual impairment. Eye angiogenesis is associated with a wide range of diseases, including wet age-related macular degeneration (wet AMD), diabetic retinopathy, macular edema, etc.

Many drugs for treating angiogenesis-related disorders have been developed, such as anti-VEGF antibodies (such as Lucentis) or fusion proteins (such as Eylea). However, frequently repeated injections are required to maintain efficacy due to short half-lives of these drugs. Therefore, new therapies targeting angiogenesis are needed for the treatment of eye diseases related to angiogenesis.

SUMMARY

Currently, there is a need in the art to develop compositions and methods that can effectively treat eye diseases associated with angiogenesis.

In some aspects, the present disclosure provides a composition comprising a first polynucleotide comprising a first sequence operably linked to a first promoter and a second sequence operably linked to a second promoter, wherein the first sequence encodes an adeno-associated virus (AAV) capsid protein, wherein the second sequence encodes an AAV rep protein, and a second polynucleotide comprising a third sequence operably linked to a third promoter, wherein the third sequence comprises a codon-optimized nucleic acid sequence encoding a Vascular Endothelial Growth Factor (VEGF) inhibitor.

In some embodiments, the VEGF inhibitor is a fusion protein, or a VEGF antibody or antigen-binding fragment thereof. In some embodiments, the codon-optimized nucleic acid sequence encodes a protein comprising an amino acid sequence of SEQ ID NO: 1, SEQ ID NO: 2, SEQ ID NO: 3, or SEQ ID NO: 4. In some embodiments, the codon-optimized nucleic acid sequence encodes a protein comprising an amino acid sequence of SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, the codon-optimized nucleic acid sequence encoding a protein comprising an amino acid sequence of SEQ ID NO: 1. In some embodiments, the codon-optimized nucleic acid sequence comprises an altered number of CpG dinucleotides than SEQ ID NO: 13. In some embodiments, the codon-optimized nucleic acid sequence comprises less than 60, 55, 50, 45, 40, 35, 30, 25, 20, 15, 10, or 5 CpG dinucleotides. In some embodiments, the codon-optimized nucleic acid sequence does not comprise CpG dinucleotides. In some embodiments, the third sequence comprises a sequence of SEQ ID NO: 14, SEQ ID NO: 15, or SEQ ID NO: 16. In some embodiments, the first promoter and the second promoter are suitable for expression in insect cells or mammalian cells. In some embodiments, the insect cells are Sf9 cells. In some embodiments, the mammalian cells are HEK293 cells or derivative cells thereof. In some embodiments, the derivative cells are HEK293T cells. In some embodiments, the first promoter or the second promoter is the p10 promoter or the polh promoter. In some embodiments, the third promoter is the CMV promoter, CAG promoter, MNDU3 promoter, PGK promoter, EF1a promoter, or an eye specific promoter. In some embodiments, the eye-specific promoter is selected from the group consisting of RPE 65 gene promoter, human retinal binding protein gene promoter, murine 11-cis retinoid alcohol dehydrogenase gene promoter, rhodopsin promoter, rhodoposin kinase promoter, tissue inhibitor of metalloproteinase 3 promoter, photoreceptor retinol binding protein promoter, vitelliform macular dystrophy 2 promoter, and interphotoreceptor retinoid-binding protein promoter. In some embodiments, the 3' end of the first sequence, the second sequence, or the third sequence further comprises a poly A sequence. In some embodiments, the poly A sequence is hGH poly(A), SV40 poly(A), or β-globin poly(A). In some embodiments, the first sequence and the second sequence are connected by a linker. In some embodiments, the linker is a cleavable linker. In some embodiments, the linker comprises a 2A peptide. In some embodiments, the linker comprises an internal ribosome entry site (IRES). In some embodiments, the IRES is from Foot and Mouth Disease virus (FMDV). In some embodiments, the second polynucleotide comprises an intron or a regulatory element. In some embodiments, the intron comprises a chimeric intron. In some embodiments, the regulatory element comprises a TPL (the tripartite leader sequence from adenovirus) and an eMLP (enhancer element from the adenovirus major late promoter) sequence. In some embodiments, the second polynucleotide comprises a Kozak sequence. In some embodiments, the second polynucleotide comprises a human scaffold-attached region (SAR) sequence. In some embodiments, the second polynucleotide further comprises an enhancer. In some embodiments, the enhancer is the CMV enhancer. In some embodiments, the second polynucleotide further comprises a filler sequence. In some embodiments, the second polynucleotide further comprises inverted terminal repeat (ITR) sequences. In some embodiments, the ITR sequences are AAV2 ITRs. In some embodiments, the second polynucleotide further comprises a fourth sequence encoding an additional therapeutic protein. In some embodiments, the additional therapeutic protein is selected from the group consisting of VEGF inhibitors, PDGF inhibitors, placental growth factor inhibitors, integrin inhibitors, mTOR inhibitors, angiopoietin inhibitors, and TGFB inhibition agent. In some embodiments, the third sequence and the fourth sequence are connected by a linker. In some embodiments, the linker is a cleavable linker. In some embodiments, the linker comprises a 2A peptide.

In another aspect, the present disclosure provides a recombinant adeno-associated virus (rAAV) particle prepared by introducing any of the polynucleotides disclosed herein or any of the compositions disclosed herein into cells. In some embodiments, the cells are insect cells or mammalian cells. In some embodiments, the insect cells are Sf9 cells. In some embodiments, the mammalian cells are HEK293 cells or derivative cells thereof. In some embodiments, the derivative cells are HEK293T cells.

In another aspect, the present disclosure provides a polynucleotide, comprising a codon-optimized nucleic acid sequence encoding a protein comprising an amino acid sequence of SEQ ID NO: 1, SEQ ID NO: 2, SEQ ID NO: 3, or SEQ ID NO: 4. In some embodiments, the codon-optimized nucleic acid sequence encoding a protein comprising an amino acid sequence of SEQ ID NO: 1. In some embodiments, the codon-optimized nucleic acid sequence comprises an altered number of CpG dinucleotides than SEQ ID NO: 13. In some embodiments, the codon-optimized nucleic acid sequence comprises less than 60, 55, 50, 45, 40, 35, 30, 25, 20, 15, 10, or 5 CpG dinucleotides. In some embodiments, the codon-optimized nucleic acid sequence does not comprise CpG dinucleotides. In some embodiments, the third sequence comprises a sequence of SEQ ID NO: 14, SEQ ID NO: 15, or SEQ ID NO: 16. In some embodiments, the polynucleotide further comprises a promoter. In some embodiments, the promoter is the CMV promoter, CAG promoter, MNDU3 promoter, PGK promoter, EF1a promoter, or an eye specific promoter. In some embodiments, the eye-specific promoter is selected from the group consisting of RPE 65 gene promoter, human retinal binding protein gene promoter, murine 11-cis retinoid alcohol dehydrogenase gene promoter, rhodopsin promoter, rhodoposin kinase promoter, tissue inhibitor of metalloproteinase 3 promoter, photoreceptor retinol binding protein promoter, vitelliform macular dystrophy 2 promoter, and interphotoreceptor retinoid-binding protein promoter. In some embodiments, the polynucleotide further comprises a poly A sequence. In some embodiments, the poly A sequence is hGH poly(A), SV40 poly(A), or β-globin poly(A). In some embodiments, the polynucleotide further comprises an intron or a regulatory element. In some embodiments, the intron comprises a chimeric intron. In some embodiments, the regulatory element comprises a TPL (the tripartite leader sequence from adenovirus) and an eMLP (enhancer element from the adenovirus major late promoter) sequence. In some embodiments, the polynucleotide further comprises a Kozak sequence.

In another aspect, the present disclosure provides a recombinant adeno-associated virus (rAAV) particle, comprising any of the polynucleotides disclosed herein.

In another aspect, the present disclosure provides a method for expressing a VEGF inhibitor in a cell or a tissue of a subject, comprising administering to the cell or the tissue of the subject any of the rAAV particles disclosed herein or any of the polynucleotides disclosed herein.

In another aspect, the present disclosure provides a method for treating eye diseases in a subject in need thereof, comprising administering to the subject a therapeutically effective amount of any of the rAAV particles disclosed herein or any of the polynucleotides disclosed herein. In some embodiments, the ocular disease is selected from the group consisting of wet age-related macular degeneration (wet AMD), diabetic retinopathy, diabetic macular edema, proliferative diabetic retinopathy, and macular edema.

In another aspect, the present disclosure provides a method for preparing a recombinant adeno-associated virus (rAAV) particle, comprising introducing a cell with any of the compositions disclosed herein or any of the polynucleotides disclosed herein. In some embodiments, the method comprising expressing any of the polynucleotides disclosed herein in the cell. In some embodiments, the cell is an insect cell or a mammalian cell. In some embodiments, the insect cell is the Sf9 cell. In some embodiments, the mammalian cell is the HEK293 cell or a derivative cell thereof. In some embodiments, the derivative cell is the HEK293T cell. In some embodiments, the method comprises generating bacmid DNA and/or baculovirus. In some embodiments, the method comprises generating bacmid DNA comprising the VEGF inhibitor expression sequence (such as the polynucleotides disclosed herein). In some embodiments, the method comprises generating bacmid DNA rAAV cap-rep expression sequence. In some embodiments, the method comprises transfecting a cell with the bacmid DNA to produce baculoviruses. In some embodiments, the method comprises transfecting a cell with the bacmid DNA comprising the VEGF inhibitor expression sequence to produce baculoviruses. In some embodiments, the method comprises transfecting a cell with the bacmid DNA to produce baculoviruses comprising the rAAV cap-rep expression sequence. In some embodiments, the method further comprises mixing the baculoviruses to infect a cell (such as the Sf9 cell) to obtain packaged rAAV/VEGF inhibitor virus particles disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
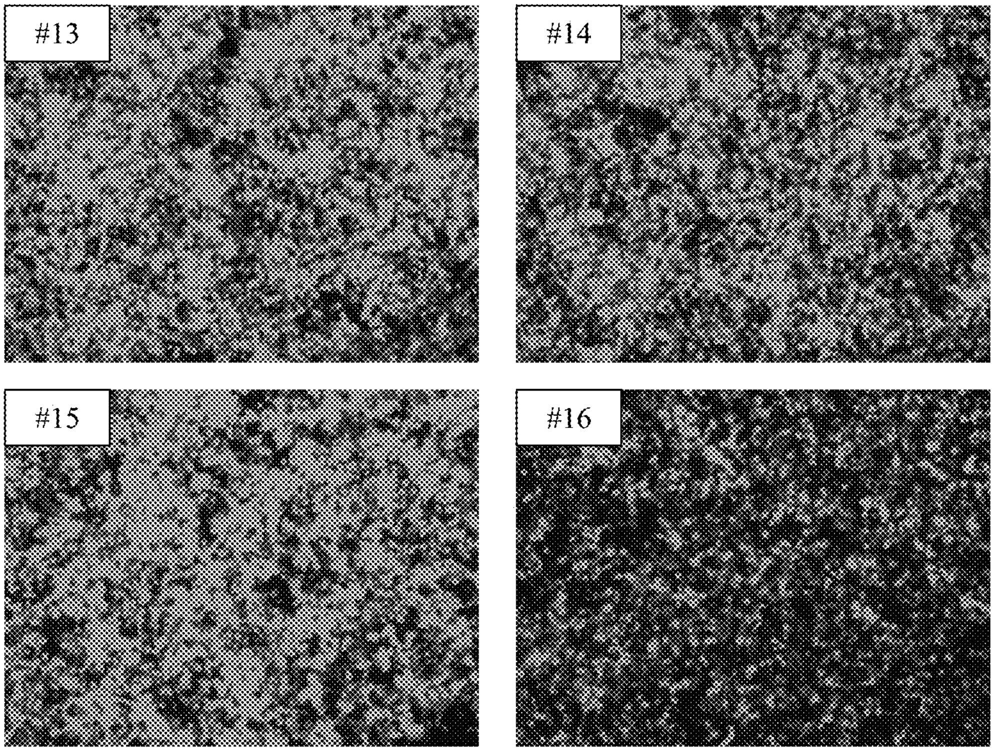
FIG. 1A illustrates the fluorescent images showing the expression of green fluorescent protein (GFP) 48 hours after transfection of the second polynucleotide encoding GFP in 293T cells.

Although various embodiments of the present invention have been shown and described herein, it will be apparent to those skilled in the art that these embodiments are provided by way of example only. Those skilled in the art can think of many variations, changes, and substitutions without departing from the invention. It should be understood that various alternatives to the embodiments of the invention described herein may be employed.

Unless otherwise stated, the practice of some embodiments disclosed herein employs conventional techniques of immunology, biochemistry, chemistry, molecular biology, microbiology, cell biology, genomics, and recombinant DNA. For example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PC 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Definition

As used in the specification and claims, the singular forms "a", "an" and "said" include plural references unless the context clearly dictates otherwise. For example, the term "immunoactivator" includes one or more immune activators.

The term "about" or "approximately" means within an acceptable error range for a particular value determined by one of ordinary skill in the art, which will depend in part on how the value is measured or determined, that is, the limitations of the measurement system. For example, according to practice in the art, "about" may be expressed within a standard deviation of 1 or greater. Alternatively, "about" may mean a range of up to 20%, up to 10%, up to 5%, or up to 1% of a given value. Or, especially for biological systems or processes, the term may mean an order of magnitude of the value, preferably within 5 times, more preferably within 2 times. Where specific values are described in the application and claims, unless otherwise stated, it should be assumed that the term "about" means within an acceptable error range for the specific value.

The term "treatment" as used herein refers to an attempt to alter the natural course of treatment of a disease in an individual and may be clinical intervention for prevention or implementation during the course of clinical pathology. The desired effects of treatment include but are not limited to preventing the occurrence or recurrence of the disease, relieving symptoms, reducing any direct or indirect pathological consequences of the disease, preventing metastasis, slowing the rate of disease progression, improving or reducing the disease state and/or improving prognosis.

As used herein, the terms "polypeptide", "peptide" and "protein" are used interchangeably herein to refer to an amino acid polymer of any length. The polymer may be linear, cyclic, or branched, it may contain modified amino acids, and it may be interrupted by non-amino acids. The term also includes amino acid polymers that have been modified, such as by sulfation, glycosylation, lipidation, acetylation, phosphorylation, iodination, methylation, oxidation, proteolytic treatment, phosphorylation, isoprenylation, racemization, selenization, transfer RNA-mediated addition of amino acids to proteins (e.g., arginine), ubiquitination, or any other manipulations, such as conjugation with labeled components. As used herein, the term "amino acid" refers to natural and/or unnatural or synthetic amino acids, including glycine and D or L optical isomers, as well as amino acid analogs and peptidomimetics. A polypeptide or amino acid sequence "derived" from a specified protein refers to the origin of the polypeptide. Preferably, the polypeptide has an amino acid sequence substantially the same as the amino acid sequence of the polypeptide encoded in the sequence, or a portion thereof, wherein the portion consists of at least 10-20 amino acids or at least 20-30 amino acids or at least 30-50 amino acids, or it can be identified immunologically with the polypeptide encoded in the sequence. The term also includes polypeptides expressed from specified nucleic acid sequences. As used herein, the term "domain" refers to a part of a protein that is physically or functionally distinguished from other parts of the protein or peptide. Physically defined domains include very hydrophobic or hydrophilic amino acid sequences, such as those membrane-bound or cytoplasmic-bound sequences. Domains can also be defined by, for example, internal homology caused by gene replication. Functionally defined domains have different biological functions. For example, the antigen-binding domain refers to the part of the antigen-binding unit or antibody that binds to the antigen. Functionally defined domains need not be encoded by consecutive amino acid sequences, and functionally defined domains may contain one or more physically defined domains.

As used herein, the term "amino acid" refers to natural and/or unnatural or synthetic amino acids, including but not limited to D or L optical isomers, as well as amino acid analogs and peptidomimetics. Standard one-letter or three-letter codes are used to refer to amino acids. In this context, amino acids are generally represented by one-letter and three-letter abbreviations known in the art. For example, alanine can be represented by A or Ala.

As used herein, in the case of a polypeptide, the "sequence" is the sequence of amino acids in the polypeptide in the direction from the amino terminus to the carboxy terminus, wherein the residues adjacent to each other in the sequence are in the polypeptide. The primary structure is continuous. The sequence may also be a linear sequence of a part of a polypeptide known to contain additional residues in one or two directions.

As used herein, "identity", "homology" or "sequence identity" refers to sequence similarity between two or more polynucleotide sequences or between two or more polypeptide sequences. When using programs such as EMBOSS Needle or BestFit to determine the sequence identity, similarity, or homology between two different amino acid sequences, the default settings can be used, or an appropriate scoring matrix, such as blosum45 or blosum80, can be selected for optimization identity, similarity or homology score. Preferably, homologous polynucleotides are those that hybridize under stringent conditions and have at least 70%, preferably at least 80%, more preferably at least 90%, more preferably 95%, more preferably 97%, more preferably 98% and even more preferably 99% sequence identity compared to these sequences. When optimally aligning sequences of comparable length, homologous polypeptides preferably have at least 80%, or at least 90%, or at least 95%, or at least 97%, or at least 98% sequence identity, or have at least 99% sequence identity.

As far as the antigen binding unit disclosed herein is concerned, the term "percent sequence identity (%)" is defined as the percentage of the same animo acid between the query sequence and the second and reference polypeptide sequences after aligning the sequences and introducing gaps as necessary to obtain the maximum percentage of sequence identity, without considering any conservative substitutions as part of sequence identity. The alignment for determining the percent identity of amino acid sequences can be achieved in various ways appreciated by the skilled in the art, for example by using publicly available computer software, such as BLAST®, BLAST-2®, ALIGN®, NEEDLER or Megalign (DNASTAR®). Those skilled in the art can determine suitable parameters for measuring alignment, including any algorithms needed to obtain maximum alignment over the full length of the sequences to be compared. The percent identity can be measured over the length of the entire defined polypeptide sequence, or can be measured over a shorter length, for example, over the length of a fragment taken from a larger defined polypeptide sequence, such as fragments of at least 5, at least 10, at least 15, at least 20, at least 50, at least 100 or at least 200 consecutive residues. These lengths are only exemplary and it should be understood that any fragment length supported by the sequence shown in the table, figure, or sequence listing herein can be used to describe the length on which the percent identity can be measured.

The proteins described herein may have one or more modifications relative to a reference sequence. The modification may be a deletion, insertion or addition, or substitution of amino acid residues. "Deletion" refers to a change in the amino acid sequence due to the removal of one or more amino acid residues. "Insertion" or "addition" refers to an amino acid sequence change that results in the addition of one or more amino acid residues compared to the reference sequence. "Substitution" or "substituted" means that one or more amino acids are replaced with different amino acids. Here, the mutation of the antigen binding fragment as compared to the reference sequence can be determined by comparing the antigen binding fragment with the reference sequence. The optimal alignment of sequences for comparison can be performed according to any known method in the art.

As used herein, the term "isolated" refers to separation from cellular and other components, where in nature, polynucleotides, peptides, polypeptides, proteins, antibodies or fragments thereof. Those skilled in the art are aware that non-naturally occurring polynucleotides, peptides, polypeptides, proteins, antibodies or fragments thereof need not be "isolated" to distinguish them from their naturally occurring counterparts. In addition, "concentrated", "isolated" or "diluted" polynucleotides, peptides, polypeptides, proteins, antibodies or fragments thereof are distinguishable from their naturally occurring counterparts because of the concentration or number of molecules per unit volume greater than ("concentrated") or smaller than its naturally occurring counterpart ("isolated"). Enrichment can be measured based on absolute amounts, such as the weight of the solution per unit volume, or it can be measured relative to the second, potentially interfering substance present in the source mixture.

The terms "polynucleotide", "nucleic acid", "nucleotide" and "oligonucleotide" are used interchangeably. They refer to polymeric forms of nucleotides of any length (whether deoxyribonucleotides or ribonucleotides) or their analogs. Polynucleotides can have any three-dimensional structure and can perform any known or unknown function. The following are non-limiting examples of polynucleotides: coding or non-coding regions of genes or gene fragments, loci determined from linkage analysis, exons, introns, messenger RNA (mRNA), transfer RNA, ribosomes RNA, ribozyme, cDNA, recombinant polynucleotide, branched polynucleotide, plasmid, vector, isolated DNA, isolated RNA, nucleic acid probe, primer, oligonucleotide or synthetic DNA. The polynucleotide may comprise modified nucleotides, such as methylated nucleotides and nucleotide analogs. Modifications to the nucleotide structure can be imparted before or after formation of polynucleotides. The sequence of nucleotides may be interrupted by non-nucleotide components. The polynucleotide can be further modified after polymerization, for example by conjugation with a labeling component.

When applied to a polynucleotide, "recombinant" means that the polynucleotide is a cloning or a product resulted from restriction digestion and/or ligation and other procedures and the product is different from the polynucleotide found in nature.

The terms "gene" or "gene fragment" are used interchangeably herein. They refer to polynucleotides containing at least one open reading frame that can encode a specific protein after transcription and translation. The gene or gene fragment may be genomic, cDNA, or synthetic, as long as the polynucleotide contains at least one open reading frame, which may cover the entire coding region or segment thereof.

The term "operably connected" or "effectively connected" refers to juxtaposition of components that allows the components to function in their intended manner. For example, if the promoter sequence promotes the transcription of the coding sequence, the promoter sequence is operably linked to the coding sequence.

As used herein, "expression" refers to the process by which a polynucleotide is transcribed into mRNA and/or the process by which the transcribed mRNA (also referred to as a "transcript") is subsequently translated into a peptide, polypeptide, or protein. Transcripts and encoded polypeptides are collectively referred to as gene products. If the polynucleotide is derived from genomic DNA, expression may include splicing of mRNA in eukaryotic cells.

As used herein, the term "vector" refers to a nucleic acid vehicle into which a polynucleotide can be inserted. When the vector enables expression of the protein encoded by the inserted polynucleotide, the vector is called an expression vector. The vector can be introduced into the host cell by transformation, transduction or transfection, such that the genetic material carried by it can be expressed in the host cell. Vectors well known to those skilled in the art include, but are not limited to, plasmids, phagemids, artificial chromosomes such as yeast artificial chromosomes (YAC), bacterial artificial chromosomes (BAC), and P1 derived artificial chromosomes (PAC), phages such as lambda Phage and M13 phage, and animal viruses. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papillae polyoma vacuolar virus (eg SV40). A vector can have multiple elements to control expression, including but not limited to, promoters, transcription initiators, enhancers, selection elements, and reporter genes. In addition, the vector may also contain an origin of replication.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

As used herein, the term "antibody" refers to an immunoglobulin molecule that generally consists of two pairs of polypeptide chains (each pair having one "light" (L) chain and one "heavy" (H) chain). Antibody light chains can be classified into kappa and lambda light chains. Heavy chains can be classified as μ, δ, γ, α, or ε, and the antibody isotypes are defined as IgM, IgD, IgG, IgA, and IgE, respectively. Within the light and heavy chains, the variable and constant regions are connected by a "J" region of about 12 or more amino acids, and the heavy chain also contains a "D" region of about 3 or more amino acids. Each heavy chain is composed of a heavy chain variable region (VH) and a heavy chain constant region (CH). The heavy chain constant region is composed of 3 domains (CH1, CH2 and CH3). Each light chain is composed of a light chain variable region (VL) and a light chain constant region (CL). The light chain constant region consists of a domain CL. The constant region of the antibody may mediate the binding of the immunoglobulin to host tissues or factors, including various cells of the immune system (e.g., effector cells) and the first component (C1q) of the classical complement system. The VH and VL regions can also be subdivided into regions with high denaturation (referred to as complementarity determining regions (CDR)), with more conserved regions called framework regions (FR) interspersed therebetween. Each VH and VL consists of 3 CDRs and 4 FRs arranged in the following order: FR1, CDR1, FR2, CDR2, FR3, CDR3, FR4 arranged from amino terminus to carboxy terminus. The variable regions (VH and VL) of each heavy/light chain pair form antibody binding sites, respectively. The allocation of amino acids to each region or domain follows Kabat Sequences of Proteins of Immunological Interest (National Institutes of Health, Bethesda, Md. (1987 and 1991)), or Chothia & Lesk (1987) J. Mol. Biol. 196:901-917; definition of Chothia et al. (1989) Nature 342:878-883. The term "antibody" is not limited by any particular method of producing antibodies. For example, it includes recombinant antibodies, monoclonal antibodies and polyclonal antibodies. The antibodies may be antibodies of different isotypes, for example, IgG (eg, IgG1, IgG2, IgG3 or IgG4 subtypes), IgA1, IgA2, IgD, IgE or IgM antibodies.

As used herein, the term "antigen-binding fragment" of an antibody refers to a polypeptide comprising a fragment of a full-length antibody that retains the ability to specifically bind the same antigen to which the full-length antibody binds, and/or the ability to compete with long antibodies to specifically bind to antigens. An antigen-binding fragment is also known as an "antigen-binding portion". See generally, Fundamental Immunology, Ch. 7 (Paul, W., ed., 2nd edition, Raven Press, NY (1989), which is incorporated herein by reference in its entirety for all purposes. Using recombinant DNA technology, enzymatic fragmentation or chemical fragmentation of intact antibodies can produce antigen-binding fragments of antibodies. In some cases, antigen-binding fragments include Fab, Fab', F(ab')2, Fd, Fv, dAb and complementarity determining region (CDR) fragments, single chain antibodies (e.g., scFv), chimeric antibodies, diabodies (diabody), and polypeptides that contain at least a portion of an antibody that is sufficient to confer specific antigen-binding ability. In some cases, the antigen-binding fragments are single-chain antibodies (e.g., scFv), where the VL and VH domains are paired to form a monovalent molecule by allowing them to produce a linker that is a single polypeptide chain (see, e.g., Bird et al., Science 242:423 426 (1988) And Huston et al., Proc. Natl. Acad. Sci. USA 85:5879 5883 (1988)). Such scFv molecules may have a general structure: NH2-VL-linker-VH—COOH or NH2-VH-linker-VL-COOH. Suitable linkers include but not limited to repeated GGGGS (SEQ ID NO: 19) amino acid sequences or variants thereof. For example, linkers with amino acid sequence (GGGGS) 4 (SEQ ID NO: 20) and variants thereof can be used (See Holliger et al. (1993), Proc Natl. Acad. Sci. USA 90:6444-6448). Other linkers that can be used are described by Alfthan et al. (1995), Protein Eng. 8:725-731, Choi et al. (2001), Eur. J Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. All references are incorporated herein by reference in their entirety for all purposes.

Antigen-binding fragments of an antibody (for example, antibody fragments as mentioned above) can be obtained by routine technologies (e.g., recombinant DNA technology, enzymatic fragmentation or chemical fragmentation) and can be screened specifically in the same manner as for intact antibodies. Unless the context clearly indicates otherwise, when referring to the term "antibody", it includes not only whole antibodies but also antigen-binding fragments of the antibodies.

As used herein, the term "host cell" refers to a cell to which a vector can be introduced, which includes, but is not limited to, prokaryotic cells such as *E. coli* or *Bacillus subtilis*, fungal cells such as yeast cells or *Aspergillus*, insect cells such as S2 fruit fly cells or Sf9 insect cells, or animal cells such as fibroblasts, CHO cells, COS cells, NSO cells, HeLa cells, BHK cells, HEK293 cells, or human cells.

The terms "antagonist" and "inhibitor" are used interchangeably herein and refer to a molecule capable of inhibiting the biological function of a target protein by inhibiting the activity or expression of the target protein. Therefore, the terms "antagonist" and "inhibitor" are defined in the context of the biological effects of the target protein. Although the preferred antagonist herein specifically interacts (e.g., binds) with the target, molecules that inhibit the biological activity of the target protein by interacting with other members of the signalling pathway where the target protein is a member are also included in this definition.

As used herein, an "effective amount" refers to at least the minimum amount required to achieve a measurable improvement or prevention of a particular disease or condition. The effective amount can vary based on the patient's disease state, age, gender, and weight. The effective amount is also an amount that the therapeutic beneficial effect exceeds any toxic or adverse effects of the treatment. In the treatment of cancer or tumors, the effective amount of the drug may have the following effects: reducing the number of cancer cells, reducing the size of the tumor, inhibiting the infiltration of cancer cells into peripheral organs, inhibiting tumor metastasis, inhibiting tumor growth to some extent and/or alleviating one or more symptoms related to the disease to some extent. The effective amount can be administered in one or more applications.

As used herein, the terms "recipient", "individual", "subject", "host" and "patient" are used interchangeably and refer to any mammalian subject to be diagnosed or treated, preferably a human.

As used herein, the terms "treatment", "treating" and the equivalent are used herein to generally refer to obtaining the desired pharmacological and/or physiological effect. The effect may be preventive in terms of completely or partially preventing the disease or its symptoms, and/or may be therapeutic in terms of partially or completely stabilizing or curing the disease and/or adverse reactions attributed to the disease. "Treatment" as used herein encompasses any treatment of diseases in mammals such as mice, rats, rabbits, pigs, primates, including humans and other apes, preferably humans. The term includes the following: (a) preventing the disease or symptom from occurring in subjects who may be susceptible to the disease or symptom but the diagnosis has not yet occurred; (b) inhibiting the disease symptom; (c) preventing development of the disease; (d) relieving symptoms of the disease; (e) cause the disease or symptoms to subside; or any combination of (a)-(e).

The term "kit" as used herein refers to a combination packaged for common use or commercially available. For example, the kit of the present disclosure may contain the composition disclosed herein and the instructions for using the composition or kit. The term "instructions" refers to the explanatory inserts usually contained in commercial packages of therapeutic products, which contain information about indications, use, dosage, administration, combination therapy, contraindications and/or warnings about the use of such therapeutic products.

The term "codon optimization" or "codon-optimized" refers to changing the codons that make up a nucleic acid sequence so that the codons are most suitable for expression in a specific system (e.g., a specific species or a group of species). For example, a nucleic acid sequence is optimized for more efficient expression in mammalian cells. Due to the existence of synonymous codons, codon optimization does not change the amino acid sequence of the encoded protein. A variety of codon optimization methods are known in the art, such as those disclosed in U.S. Pat. Nos. 5,786,464 and 6,114,148, which are incorporated herein by reference in their entirety for all purposes. "Synonymous codons" refer to codons that encode the same amino acid.

There are 20 amino acids that make up a protein, and 64 codons that encode amino acids. Each amino acid corresponds to at least one codon, and one amino acid can correspond to up to 6 codons (degenerate codons). Different organisms, even different protein-coding genes of the same organism, have different frequency of use of degenerate codons and have a certain preference. Among them, codons with high frequency are called preferred codons, and those that are rarely used are called rare or low-frequency codons. Optimization of gene codons can increase protein expression level by utilizing preferred codons, avoiding rare or low-frequency codons with low utilization, simplifying the secondary structure of mRNA after gene transcription, incorporating motifs that are conducive to high-efficiency expression and reducing motifs that are unfavorable to expression, and adjusting GC content, and the like. Although there are many general codon optimization principles, these general optimization principles cannot be uniformly applied to a single gene therapy vector. Different general optimization principles may contradict each other. For example, changing the composition of CpG islands or the GC content of the coding region may affect the choice of codon usage preference. In addition, different codon optimizations may lead to different post-translational modifications and different biological activities.

"Active" or "activity" for purposes of the present invention refers to forms of a therapeutic protein which retain a biological activity of the corresponding native or naturally occurring polypeptide. The activity may be greater than, equal to, or less than that observed with the corresponding native or naturally occurring polypeptide.

Wet Macular Degeneration

The macula is the central part of the retina. Macular degeneration, also known as retinal degeneration, is an eye disease involving macular degeneration.

Age-related macular degeneration (AMD) is one of the most important causes of irreversible visual impairment in people over the age of 50. AMD is clinically divided into two types, "dry" and "wet". In the wet form of AMD, new blood vessels form and change the blood supply to retinal tissues, especially those below the macula. However, new blood vessels are easily damaged, and their rupture will cause bleeding and injury to the surrounding tissues, retinal tissue scarring formation, and rapid loss of vision. The disease progresses rapidly and often leads to blindness. Wet macular degeneration usually begins with distortion in the center of the visual field, accounting for about 90% of the blindness associated with macular degeneration.

Several cytokines have been found to play an important role in the regulation of angiogenesis, including but not limited to, vascular endothelial growth factor (VEGF), VEGF receptor (VEGFR), placental growth factor, platelet-derived growth factor (PDGF), hypoxia inducible factor (HIF), angiopoietin (Ang) and other cytokines, and mitogen-activated protein kinase (MPK).

Vascular endothelial growth factor (VEGF) is a glycoprotein with a size of 46 kDa, which is expressed in ocular cells including pigment epithelial cells, pericytes, vascular endothelial cells, glial, and ganglion cells. VEGF is known to be associated with a variety of eye diseases, including but not limited to, ischemic retinopathy, intraocular neovascularization, age-related macular degeneration (AMD), wet AMD, dry AMD, retinal neovascularization, diabetes macular edema, diabetic retinal ischemia, diabetic retinal edema, proliferative diabetic retinopathy, retinal vein occlusion, central retinal vein occlusion, branch retinal vein occlusion.

Eylea® (aflibercept), an VEGF-binding fusion protein, is a drug approved for the treatment of wet AMD. It can prevent ocular neovascularization and thus treat wet AMD. Lucentis® (ranibizumab) an anti-VEGF antibody, is another drug approved for the treatment of wet AMD. It also can prevent ocular neovascularization and thus treat wet AMD. Clinical studies have shown that about 95% of patients administered Lucentis® have improved or stable vision. However, both drugs are very expensive and frequently repeated injections are required to maintain efficacy due to short half-lives of these drugs. Therefore, new therapies are needed for targeting VEGF to treat related eye diseases.

Recombinant AAV Vector

Adeno-associated virus (AAV) belongs to the Parvoviridae family and is a single-stranded DNA (ssDNA) virus. The AAV genome is about 4.7 kilobases in length and contains inverted terminal repeats (ITRs) at both ends of the DNA strand and two open reading frames (ORFs) called rep and cap.

The "AAV inverted terminal repeat (ITR)" sequence is a sequence of about 145 nucleotides present at both ends of the native single-stranded AAV genome. The ITR is a symmetrical nucleic acid sequence for efficient replication in the adeno-associated virus genome, which can be used as a replication origin for viral DNA synthesis and is a structural component necessary for recombinant AAV vectors.

"Rep" contains polynucleotide sequences encoding the four rep proteins rep78, rep68, rep52 and rep40 that are required for the AAV life cycle. "Cap" contains the polynucleotide sequences encoding the AAV capsid proteins VP1, VP2, and VP3, where the AAV capsid proteins VP1, VP2, and VP3 can interact with each other to form a twenty-four symmetric AAV capsid.

AAV can effectively infect divided and non-divided human cells, and its genome can be integrated into a single chromosomal site in the host cell genome. Most importantly, although AAV exists in the human body, current research suggests that AAV is not associated with any disease. Based on its high safety, low immunogenicity, wide host range, and ability to mediate long-term stable expression of foreign genes in animals, AAV has become the most promising vector system for gene therapy.

Based on the AAV serotype or infected tissues or cells, 13 different AAVs have been identified so far, namely AAV1-AAV13. Moreover, as shown in Table 1 below, many advantageous vector systems using AAVs have been developed for transfection in specific cell types. Among the AAV serotypes, serotype 2 (AAV2) is the most widely studied and used. It can infect retinal epithelium, photoreceptor cells, skeletal muscle, central nerves, and liver cells. It has been used as a carrier for many clinical studies.

TABLE 1

AAV serotypes and their tissues used as carriers in gene therapy

| AAV Serotype | Delivery Organization |
|---|---|
| AAV1, AAV2, AAV4, AAV5, AAV8, AAV9 | central nervous system |
| AAV1, AAV8, AAV9 | heart |
| AAV2 | kidney |
| AAV7, AAV8, AAV9 | liver |
| AAV4, AAV5, AAV6, AAV9 | lung |
| AAV8 | pancreas |
| AAV2, AAV5, AAV8 | photoreceptor cell |
| AAV1, AAV2, AAV4, AAV5, AAV8 | retinal epithelium |
| AAV1, AAV6, AAV7, AAV8, AAV9 | skeletal muscle |

As used herein, the term "recombinant AAV vector (rAAV vector)" refers to a polynucleotide vector containing one or more heterologous sequences (i.e., non-AAV-derived nucleic acid sequences) flanked by two AAV inverted terminal repeats (ITRs). The rAAV vector can replicate and package into AAV virus particles when presenting in host cells expressing AAV rep and cap proteins.

"Recombinant AAV (rAAV) virus" or "rAAV virus particle" refers to an AAV virus particle composed of at least one AAV capsid protein encapsulating an rAAV vector. The host cells currently used for the production of rAAV virus particles are all cell types from mammals, such as 293 cells, COS cells, HeLa cells, KB cells and other mammalian cell lines. The rAAV virus particles can be produced in the mammalian cell culture system provided with the rAAV plasmids. However, the output of most of the mammalian cell culture systems is difficult to meet the needs for clinical trials and commercial scale production. For this reason, an rAAV virus particle production system using insect cells such as Sf9 cells has recently been developed. However, to produce AAV in insect cells, some modifications must be made to obtain the correct stoichiometric ratio of AAV capsid proteins.

Baculovirus belongs to the baculovirus family and is a double-stranded circular DNA virus. Its genome size is between 90 kb-230 kb. Baculoviruses are exclusively parasitic in arthropods and known to be able to infect more than 600 insects. In 1983, Smith et al. created the first baculovirus expression system by using *Autographa californica* Multicapsid Nuclear Polyhedrosis Virus (AcMNPV) to successfully express human β-interferon in *Spodoptera frugiperda* cell line Sf9 (Mol Cell Biol, 1983, 3:2156-2165). Since then, the baculovirus expression system has been continuously improved and developed and has become a widely used eukaryotic expression system. In 2002, Urabe et al. confirmed that baculovirus-infected Sf9 insect cells can support the replication of AAV. They used three recombinant baculoviruses, carrying AAV's rep gene, cap gene and ITR core expression elements respectively, to co-infect Sf9 cells and successfully prepared rAAV virus particles. From then on, researchers have continuouly developed systems that are more suitable for large-scale preparation of rAAV virus particles.

At present, there are two main baculovirus expression systems for large-scale preparation of rAAV virus particles: the two-baculovirus system (Two Bac system) and the packaging cell line-dependent one-baculovirus system (One Bac system). The main process of preparing rAAV virus particles using the two-baculovirus system is to integrate the rep gene and the cap gene of AAV in one baculovirus genome, and integrate the ITR core expression element and the target gene of interest into another baculovirus genome. The two recombinant baculoviruses are then used to co-infect the host cells to produce rAAV virus particles carrying the gene of interest. The main process for preparing rAAV virus particles using one-baculovirus system starts with establishing a packaging cell line that induces the expression of rep and cap genes. The packaging cell line integrates rep and cap gene expression elements such that the rep gene and the cap gene were placed under the control of the baculovirus late gene expression strong promoter polh promoter. An hr2 enhancer sequence and an AAV rep protein binding sequence can be further added upstream of the polh promoter. After infection with the recombinant baculovirus containing the AAV ITR and the target gene, the rep gene and cap gene in the packaging cell line are induced to express proteins, thereby generating rAAV virus particles integrating the target gene.

In some embodiments, the rAAV vector used to carry the gene of interest in the rAAV viral particles may further include one or more "expression regulatory elements." The term "expression regulatory element" as used herein refers to a nucleic acid sequence that affects the expression of an operably linked polynucleotide, including polynucleotide sequences that promote the transcription and translation of heterologous polynucleotides. Non-limiting examples of expression control elements include, but are not limited to, promoters, enhancers, intron splice signals, polyadenylation (poly(A)), inverted terminal repeat sequences (ITR). In some embodiments, the poly(A) sequence is hGH poly(A), SV40 poly(A), or β-globin poly(A).

A "promoter" is a DNA sequence located adjacent to a heterologous polynucleotide sequence encoding a target product, which is usually operably linked to an adjacent sequence such as a heterologous polynucleotide. The promoter generally increases expression level of the heterologous polynucleotide as compared to the expression level of the heterologous polynucleotide in the absence of the promoter.

An "enhancer" is a sequence that enhances the activity of a promoter. Unlike promoters, enhancers do not have promoter activity, and can generally function independent of their position relative to the promoter (i.e., upstream or downstream of the promoter). Non-limiting examples of enhancer elements (or portions thereof) include baculovirus enhancers and enhancer elements found in insect cells.

A "Filler sequence" refers to a nucleotide sequence contained in a larger nucleic acid molecule such as a vector and is generally used to create the required spacing between two nucleic acid sequences, such as between a promoter and a coding sequence, or to extend the nucleic acid sequence to a desired length. The filler sequence does not contain protein coding information. The filler sequence may have unknown or synthetic origin and/or be unrelated to other nucleic acid sequences in the larger nucleic acid molecule.

Composition

In one aspect, the present disclosure provides a composition comprising a first polynucleotide and a second polynucleotide, wherein the first polynucleotide comprises a first sequence operably linked to a first promoter and a second sequence operably linked to a second promoter.

In some embodiments, the first sequence encodes an adeno-associated virus (AAV) cap protein. The cap protein may be any structural protein known in the art capable of forming a functional AAV capsid (i.e., capable of packaging DNA and infecting target cells). In some embodiments, the cap protein includes VP1, VP2, and VP3. In some embodiments, the cap protein need not include all of VP1, VP2, VP3, as long as it can produce a functional AAV capsid. In some embodiments, the cap protein includes VP1 and VP2. In some embodiments, the cap protein includes VP1 and VP3. In some embodiments, the cap protein includes VP2 and VP3. In some embodiments, the cap protein includes VP1. In some embodiments, the cap protein includes VP2. In some embodiments, the cap protein includes VP3.

The VP1, VP2, VP3 may be derived from any AAV serotype. In some embodiments, the VP1 may be derived from AAV serotype 1 (AAV1), AAV serotype 2 (AAV2), AAV serotype 3 (AAV3, including serotypes 3A and 3B), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV Serotype 11 (AAV11), AAV serotype 12 (AAV12), AAV serotype 13 (AAV13), AAV-Rh10, AAV-Rh74, AAV-218 and any other known AAV. In some embodiments, the VP1 is derived from the wildtype VP1 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to these wildtype VP1 proteins. In some embodiments, the VP1 is derived from the wildtype VP1 from serotype AAV1, AAV2, AAV2 variants (such as AAV2.7m8, AAV2 (quad Y-F), and AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has one or more amino acid substitutions, deletions, and/or additions.

In some embodiments, the VP2 may be derived from AAV1, AAV2, AAV2 variants (such as AAV2.7m8, AAV2 (quad Y-F), and AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the VP2 is derived from the wildtype VP2 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to these wildtype VP1 proteins. In some embodiments, the VP2 is derived from the wildtype VP2 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has one or more amino acid substitutions, deletions, and/or additions.

The VP3 may be derived from AAV1, AAV2, AAV2 variants (such as AAV2.7m8, AAV2 (quad Y-F), and AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the VP3 is derived from the wildtype VP3 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to these wildtype VP3 proteins. In some embodiments, the VP3 is derived from the wildtype VP3 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has one or more amino acid substitutions, deletions, and/or additions.

In some embodiments, the cap comprises VP1, VP2 and/or VP3 derived from AAV of the same serotype, for example, the cap may comprise VP1, VP2 and/or VP3 all derived from AAV2. In some embodiments, the cap includes VP1, VP2, and/or VP3 derived from AAV of different serotypes. For example, the cap may comprise one or more of VP1, VP2 and/or VP3 derived from any of AAV1, AAV2, AAV2 variants (such as AAV2.7m8, AAV2 (quad Y-F), and AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, and AAV-2i8.

In some embodiments, the first sequence encoding the cap is operably linked to a first promoter. The first promoter may be any suitable promoter known in the art capable of driving the expression of the cap in the cell. In some embodiments, the first promoter may be a tissue-specific promoter, a constitutive promoter, or a regulated promoter. In some embodiments, the first promoter may be selected from different sources, for example, the first promoter may be a viral promoter, a plant promoter, or a mammalian promoter.

Examples of the first promoter include, but are not limited to, human cytomegalovirus (CMV) enhancer/promoter (e.g., CMV immediate early (CMV IE) enhancer/promoter), SV40 enhancer/promoter (e.g., SV40 early enhancer/promoter), JC polyoma virus promoter, myelin basic protein (MBP) or glial fibrillary acidic protein (GFAP) promoter, herpes simplex virus (HSV-1) latency-associated promoter (LAP), Lous sarcoma virus (RSV) long terminal repeat (LTR) promoter, neuron-specific promoter (NSE), platelet-derived growth factor (PDGF) promoter, hSYN, melanin aggregation hormone (MCH) promoter, CBA, matrix metalloprotein promoter (MPP), chicken β-actin Promoter, CAG, MNDU3, PGK and EF1a promoter.

In some embodiments, the first promoter is a promoter suitable for expression in mammalian cells. In some embodiments, the mammalian cells are HEK293 cells or derivative cells thereof. In some embodiments, the derivative cells are HEK293T cells. In some embodiments, the first promoter is a promoter suitable for expression in insect cells. In some embodiments, the insect cells are Sf9 cells. In some embodiments, the promoters suitable for expression in insect cells include, but are not limited to, polh promoter, p10 promoter, basic promoter, inducible promoter, E1 promoter, or ΔE1 promoter. In some embodiments, the first promoter is the polh promoter. In some embodiments, the first promoter is the p10 promoter.

In some embodiments, the 3' end of the first sequence further comprises a polyadenylation sequence (i.e., poly(A) sequence). In some embodiments, the length of the polyadenylation sequence may range from about 1 bp to 500 bp. In some embodiments, the length of the polyadenylation sequence may be, but not limited to, 1, 2, 3, 4, 5, 6, 7, 8, 9, 10, 20, 30, 50, 10, 200 or 500 nucleotides. In some embodiments, the poly(A) sequence is hGH poly(A), SV40 poly (A), or β-globin poly(A).

In some embodiments, the second sequence encodes an AAV rep protein, wherein the rep protein may be any replication protein necessary for replicating and packaging rAAV virus particles. In some embodiments, the rep proteins include rep78, rep68, rep52, and rep40. In some embodiments, the rep protein need not include all of rep78, rep68, rep52, and rep40, as long as it allows the rAAV virus particles to be replicated and packaged. In some embodiments, the rep protein includes any three of rep78, rep68, rep52, and rep40. In some embodiments, the rep protein includes any two of rep78, rep68, rep52, and rep40. In some embodiments, the rep protein includes any one of rep78, rep68, rep52, and rep40. In some embodiments, the rep protein includes rep78 and rep52. In some embodiments, the rep protein includes rep78 and rep40. In some embodiments, the rep protein includes rep68 and rep52. In some embodiments, the rep protein includes rep68 and rep40.

The rep78, rep68, rep52 and rep40 can be derived from any AAV serotype. In some embodiments, the rep78 may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the rep78 is derived from the wildtype rep78 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to the wildtype rep78 proteins. In some embodiments, the rep 78 is derived from the wildtype rep78 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-2i8, which has one or more amino acid substitutions, deletions, and/or additions.

In some embodiments, the rep68 may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the rep68 is derived from the wildtype rep68 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to the wildtype rep68 proteins. In some embodiments, the rep68 is derived from the wildtype rep68 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-2i8, which has substitution, deletion and/or addition of one or more amino acids.

In some embodiments, the rep52 may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the rep52 is derived from the wildtype rep52 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to the wildtype rep52 proteins. In some embodiments, the rep52 is derived from the wildtype rep52 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218 has one or more amino acid substitutions, deletions, and/or additions.

In some embodiments, the rep40 may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the rep40 is derived from the wildtype rep52 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218, which has at least 75%, 80%, 85%, 90%, 95% or higher identity to the wildtype rep52 proteins. In some embodiments, the rep40 is derived from the wildtype rep52 from serotype AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74 or AAV-218 has one or more amino acid substitutions, deletions, and/or additions.

In some embodiments, the rep comprises rep78, rep68, rep52 and/or rep40 derived from the same serotype AAV. For example, the rep may comprise rep78, rep68, rep52 and/or rep40 derived from AAV2 only. In some embodiments, the rep includes rep78, rep68, rep52, and/or rep40 derived from different serotypes AAV. For example, the rep may include AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and one or more of any other known AAV rep78, rep68, rep52 And/or rep40.

In some embodiments, the second sequence encoding the rep protein is operably linked to a second promoter. The second promoter may be any suitable promoter known in the art capable of driving expression of the cap in a cell. In some embodiments, the second promoter may be a tissue-specific promoter, a constitutive promoter, or a regulated promoter. In some embodiments, the second promoter may be selected from a different source. For example, the second promoter may be a viral promoter, a plant promoter, or a mammalian promoter.

Examples of the second promoter include, but are not limited to, human cytomegalovirus (CMV) enhancer/promoter (e.g., CMV immediate early (CMV IE) enhancer/promoter), SV40 enhancer/promoter (e.g., SV40 early enhancer/promoter), JC polyoma virus promoter, myelin basic Protein (MBP) or glial fibrillary acidic protein (GFAP) promoter, herpes simplex virus (HSV-1) latency-associated promoter (LAP), Lous sarcoma virus (RSV) long terminal repeat (LTR) promoter, neuron-specific promoter (NSE), platelet-derived growth factor (PDGF) promoter, hSYN, melanin aggregation hormone (MCH) promoter, CBA, matrix metalloprotein promoter (MPP), chicken β-actin promoter, CAG, MNDU3, PGK and EF1a promoter.

In some embodiments, the second promoter is a promoter suitable for expression in mammalian cells. In some embodiments, the mammalian cells are HEK293 cells or derivative cells thereof. In some embodiments, the derivative cells are HEK293T cells. In some embodiments, the second promoter is a promoter suitable for expression in insect cells. In some embodiments, the insect cells are Sf9 cells. In some embodiments, the promoters suitable for expression in insect cells include, but are not limited to, polh promoter, p10 promoter, basic promoter, inducible promoter, E1 promoter, or ΔE1 promoter. In some embodiments, the second promoter is the polh promoter. In some embodiments, the second promoter is the p10 promoter.

In some embodiments, the 3' end of the second sequence further comprises a polyadenylation sequence (i.e., a poly (A) sequence). In some embodiments, the length of the polyadenylation sequence may range from about 1 bp to 500 bp. In some embodiments, the length of the polyadenylation sequence may be, but not limited to, 1, 2, 3, 4, 5, 6, 7, 8, 9, 10, 20, 30, 50, 10, 200 or 500 nucleotides. In some embodiments, the poly(A) sequence is hGH poly(A), SV40 poly (A), or β-globin poly(A).

In some embodiments, the cap and the rep may be derived from the same AAV serotype. For example, both of the cap and rep can be derived from the same AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 or any other known AAV.

In some embodiments, the cap and the rep may be derived from different AAV serotypes. For example, the cap may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 or any other known AAV, while the rep may be derived from any of the AAV mentioned but the one which the cap derived from. For example, the cap may be derived from AAV2, while the rep is derived from AAV5.

In some embodiments, the first promoter and the second promoter may be the same promoter. For example, the first promoter and the second promoter are the same one selected from the group consisting of polh promoter, p10 promoter, basic promoter, inducible promoter, E1 promoter, and ΔE1 promoter. For example, in some embodiments, the first promoter and the second promoter are both polh promoters. In some embodiments, both the first promoter and the second promoter are p10 promoters.

In some embodiments, the first promoter and the second promoter may be different promoters. For example, the first promoter and the second promoter may be two different promoters selected from polh promoter, p10 promoter, basic promoter, inducible promoter, E1 promoter and ΔE1 promoter. For example, in some embodiments, the first promoter is the polh promoter, and the second promoter is the p10 promoter. In some embodiments, the first promoter is the p10 promoter, and the second promoter is the polh promoter.

In some embodiments, the first sequence and the second sequence are linked by a sequence encoding a linker. In some embodiments, the linker is a cleavable linker. In some embodiments, the cleavable linker is a sequence comprising a 2A peptide. In some embodiments, the 2A peptide may be selected from 2A peptides derived from the genus *Aphthora* or Cardiovirus, for example derived from foot-and-mouth disease virus (FMDV), horse rhinitis A virus (ERAV), *Thoseaasigna* virus (TaV) or 2A peptide of porcine Jieshen virus (PTV-1). In some embodiments, the linker-encoding sequence further comprises a promoter sequence. In some embodiments, the promoter is an FMDV promoter.

In some embodiments, the second polynucleotide of the composition disclosed herein comprises a third sequence comprises a codon-optimized nucleic acid sequence encoding a VEGF inhibitor. In some embodiments, the composition comprises a scAAV vector, wherein the scAAV vector comprises the second polynucleotide. In some embodiments, the composition comprises a ssAAV vector, wherein the ssAAV vector comprises the second polynucleotide.

The VEGF inhibitor may be any polypeptide or protein capable of inhibiting the biological function of VEGF protein by inhibiting the activity or expression of VEGF protein. In some embodiments, the VEGF inhibitor is an anti-VEGF antibody or antigen-binding fragment thereof. In some embodiments, the antigen-binding fragments include, but are not limited to, Fab, Fab', F(ab')2, Fd, Fv, dAb, and complementarity determining region (CDR) fragments, single-chain antibodies (scFv), chimeric antibodies and diabody. In some embodiments, the anti-VEGF inhibitor is selected from ranibizumab, bevacizumab, or aflibercept.

In some embodiments, the VEGF inhibitor comprises the sequence of SEQ ID NO: 1 or a sequence having at least 70%, 80%, 90%, 95%, 96%, 97%, 98%, or 99% homology to SEQ ID NO: 1. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 1. In some embodiments, the VEGF inhibitor comprises the sequence of SEQ ID NO: 2 or a sequence having at least 70%, 80%, 90%, 95%, 96%, 97%, 98%, 99% homology to SEQ ID NO: 2. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 2. In some embodiments, the VEGF inhibitor comprises the sequence of SEQ ID NO: 3 or a sequence having at least 70%, 80%, 90%, 95%, 96%, 97%, 98%, 99% homology to SEQ ID NO: 3. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 3. In some embodiments, the VEGF inhibitor comprises the sequence of SEQ ID NO: 4 or a sequence having at least 70%, 80%, 90%, 95%, 96%, 97%, 98%, 99% homology to SEQ ID NO: 4. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 4.

In some embodiments, the VEGF inhibitor comprises the sequence of SEQ ID NO: 5 or a sequence having at least 70%, 80%, 90%, 95%, 96%, 97%, 98%, or 99% homology to SEQ ID NO: 5. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 5. In some embodiments, the VEGF inhibitor comprises the sequence of SEQ ID NO: 6 or a sequence having at least 70%, 80%, 90%, 95%, 96%, 97%, 98%, or 99%, homology to SEQ ID NO: 6. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 6. In some embodiments, the VEGF inhibitor comprises the sequence of SEQ ID NO: 7 or a sequence having at least 70%, 80%, 90%, 95%, 96%, 97%, 98%, or 99% homology to SEQ ID NO: 7. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 7. In some embodiments, the VEGF inhibitor comprises the sequences of SEQ ID NOs: 5, 6 and 7. In some embodiments, the VEGF inhibitor comprises the sequences having at least 70%, 80%, 90%, 95%, 96%, 97%, 98%, or 99% homology to SEQ ID NOs: 5, 6 and 7. In some embodiments, the VEGF inhibitor comprises the sequences having at least 99.1%, 99.2%, 99.3%, 99.4%, 99.5%, 99.6%, 99.7%, 99.8% or 99.9% homology to SEQ ID NOs: 5, 6, and 7.

In some embodiments, the VEGF inhibitor comprises the sequence of SEQ ID NO: 8 or a sequence having at least 70%, 80%, 90%, 95%, 96%, 97%, 98%, or 99% homology to SEQ ID NO: 8. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 8. In some embodiments, the VEGF inhibitor comprises the sequence of SEQ ID NO: 9 or a sequence having at least 70%, 80%, 90%, 95%, 96%, 97%, 98%, or 99%, homology to SEQ ID NO: 9. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 9. In some embodiments, the VEGF inhibitor comprises the sequence of SEQ ID NO: 10 or a sequence having at least 70%, 80%, 90%, 95%, 96%, 97%, 98%, or 99% homology to SEQ ID NO: 10. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 10. In some embodiments, the VEGF inhibitor comprises the sequences of SEQ ID NOs: 8, 9 and 10. In some embodiments, the VEGF inhibitor comprises the sequences having at least 70%, 80%, 90%, 95%, 96%, 97%, 98%, or 99% homology to SEQ ID NOs: 8, 9 and 10. In some embodiments, the VEGF inhibitor comprises the sequences having at least 99.1%, 99.2%, 99.3%, 99.4%, 99.5%, 99.6%, 99.7%, 99.8% or 99.9% homology to SEQ ID NOs: 8, 9, and 10.

In some embodiments, the codon-optimized nucleic acid sequence encodes ranibizumab. In some embodiments, the codon-optimized nucleic acid sequence encodes bevacizumab. In some embodiments, the codon-optimized nucleic acid sequence encodes aflibercept. In some embodiments, the codon-optimized nucleic acid sequence encoding a protein comprising an amino acid sequence of SEQ ID NO: 1 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 1. In some embodiments, the codon-optimized nucleic acid sequence encoding a protein comprising an amino acid sequence of SEQ ID NO: 2 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 2. In some embodiments, the codon-optimized nucleic acid sequence encoding a protein comprising an amino acid sequence of SEQ ID NO: 3 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 3. In some embodiments, the codon-optimized nucleic acid sequence encoding a protein comprising an amino acid sequence of SEQ ID NO: 4 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 4.

In some embodiments, the codon-optimized nucleic acid sequence encoding a protein comprising an amino acid sequence of SEQ ID NO: 5 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 5. In some embodiments, the codon-optimized nucleic acid sequence encoding a protein comprising an amino acid sequence of SEQ ID NO: 6 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 6. In some embodiments, the codon-optimized nucleic acid sequence encoding a protein comprising an amino acid sequence of SEQ ID NO: 7 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 7. In some embodiments, the codon-optimized nucleic acid sequence encoding a protein comprising an amino acid sequence of SEQ ID NOs: 5, 6 and 7 or an amino acid sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NOs: 5, 6 and 7.

In some embodiments, the codon-optimized nucleic acid sequence encoding a protein comprising an amino acid sequence of SEQ ID NO: 8 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 8. In some embodiments, the codon-optimized nucleic acid sequence encoding a protein comprising an amino acid sequence of SEQ ID NO: 9 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 9. In some embodiments, the codon-optimized nucleic acid sequence encoding a protein comprising an amino acid sequence of SEQ ID NO: 10 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 10. In some embodiments, the codon-optimized nucleic acid sequence encoding a protein comprising an amino acid sequence of SEQ ID NOs: 8, 9 and 10 or an amino acid sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NOs: 8, 9 and 10.

In some embodiments, the codon-optimized nucleic acid sequence encoding a protein comprising an amino acid sequence of SEQ ID NO: 11 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 11. In some embodiments, the codon-optimized nucleic acid sequence encoding a protein comprising an amino acid sequence of SEQ ID NO: 12 or a sequence having at least 70%, 80%, 90%, 95%, 96%, 97%, 98%, 99%, 99.1%, 99.2%, 99.3%, 99.4%, 99.5%, 99.6%, 99.7%, 99.8% or 99.9% homology to SEQ ID NO: 12.

In some embodiments, the codon-optimized nucleic acid sequence comprises an altered number of CpG dinucleotide than SEQ ID NO 13. In some embodiments, the codon-optimized nucleic acid sequence comprises less CpG dinucleotide than SEQ ID NO 13. In some embodiments, the codon-optimized nucleic acid sequence comprises more CpG dinucleotide than SEQ ID NO 13. In some embodiments, the codon-optimized nucleic acid sequence comprises less than 60, 55, 50, 45, 40, 35, 30, 25, 20, 15, 10, or 5 CpG dinucleotides. In some embodiments, the codon-optimized nucleic acid sequence comprises more than 5, 10, 15, 20, 25, 30, 35, 40, 45, 50, 55, 60, 65, 70, 75, or 80 CpG dinucleotides. In some embodiments, the codon-optimized nucleic acid sequence comprises 0-80 CpG dinucleotides. In some embodiments, the codon-optimized nucleic acid sequence comprises 5-75 CpG dinucleotides. In some embodiments, the codon-optimized nucleic acid sequence comprises 10-70 CpG dinucleotides. In some embodiments, the codon-optimized nucleic acid sequence comprises 15-65 CpG dinucleotides. In some embodiments, the codon-optimized nucleic acid sequence comprises 20-60 CpG dinucleotides. In some embodiments, the codon-optimized nucleic acid sequence comprises 25-55 CpG dinucleotides. In some embodiments, the codon-optimized nucleic acid sequence comprises 30-50 CpG dinucleotides. In some embodiments, the codon-optimized nucleic acid sequence comprises 35-45 CpG dinucleotides. In some embodiments, the codon-optimized nucleic acid sequence comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30 CpG dinucleotides. In some embodiments, the codon-optimized nucleic acid sequence does not contain CpG dinucleotides. In some embodiments, the third sequence comprises a sequence of SEQ ID NO. 14, SEQ ID NO. 15, SEQ ID NO. 16, SEQ ID NO. 17, or SEQ ID NO. 18.

In some embodiments, the third sequence is operably linked to a third promoter. In some embodiments, the third promoter is the CMV promoter, CAG promoter, MNDU3 promoter, PGK promoter, EF1a promoter, or an eye-specific promoter. In some embodiments, the eye-specific promoter is a retinal pigment epithelium (RPE) cell-specific promoter. The RPE cell-specific promoters include but are not limited to RPE65 gene promoter, human retinal binding protein (CRALBP) gene promoter, murine 11-cis-retinol dehydrogenase (RDH) gene promoter, rhodopsin promoter, rhodoposin kinase promoter, tissue inhibitor of metalloproteinase 3 (Timp3) promoter, photoreceptor retinol binding protein promoter, and vitreous macular dystrophy 2 (vitelliform macular dystrophy 2) promoter, interphotoreceptor retinoid-binding protein (IRBP) promoter.

In some embodiments, the second polynucleotide further comprises other regulatory sequences, including but not limited to, inverted terminal repeats (ITR), enhancers, splicing signals, polyadenylation signals (poly(A)), stuffing sequences, terminators, protein degradation signals, internal ribosome entry elements (IRES), 2A sequences. In some embodiments, the poly(A) sequence is hGH poly(A), SV40 poly(A), or β-globin poly(A).

In some embodiments, the second polynucleotide further comprises an enhancer region. In some embodiments, the enhancer region includes an SV40 enhancer, a cytomegalovirus enhancer, an IRBP enhancer, an enhancer derived from an immunoglobulin gene. In some embodiments, the enhancer region is located upstream of the CMV, CAG, MNDU3, PGK, or EF1a promoter. In some embodiments, the enhancer is located upstream of the eye-specific promoter. In some embodiments, the enhancer region is located downstream of the CMV, CAG, MNDU3, PGK, EF1a promoter. In some embodiments, the enhancer is located downstream of the eye-specific promoter.

In some embodiments, the second polynucleotide further comprises an inverted terminal repeat sequence (ITR). In some embodiments, the second polynucleotide comprises at least one ITR. In some embodiments, the second polynucleotide comprises two ITRs. In some embodiments, the two ITRs are the same. In some embodiments, the two ITRs are different from each other. In some embodiments, the ITR is an ITR derived from AAV. In some embodiments, the ITR may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the ITR has one or more base mutations, insertions, or deletions as compared to the wildtype ITR from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218, and other known AAV, but retain the desired terminal repeat sequence functions, such as target gene replication, viruses packaging and/or integration.

In some embodiments, the second polynucleotide further comprises one or more filler sequences. In some embodiments, the filler sequence is located upstream of the CMV, CAG, MNDU3, PGK, or EF1a promoter sequence. In some embodiments, the filler sequence is located downstream of the CMV, CAG, MNDU3, PGK, or EF1a promoter sequence. In some embodiments, the filler sequence is located upstream of the eye-specific promoter. In some embodiments, the filler sequence is located downstream of the eye-specific promoter. In some embodiments, the filler sequence is located at the 5' end of the 5' ITR sequence. In some embodiments, the filler sequence is located at the 3' end of the 5' ITR sequence. In some embodiments, the filler sequence is located at the 5' end of the 3' ITR sequence. In some embodiments, the filler sequence is located at the 3' end of the 3' ITR sequence.

In some embodiments, the length of the filler sequence may be about 0.1 kb-5 kb, such as but not limited to 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb or 5.0 kb.

In some embodiments, the second polynucleotide further comprises an intron. In some cases, an intron may refer to any sequence that may be transcribed but is not translated. In some cases, an intron may refer to any sequence that be transcribed and is removed from a mature RNA transcript in a cell. In some cases, an intron may comprise about at least 1 bp, 50 bp, 100 bp, 150 bp, 200 bp, 300 bp, 400 bp, 500 bp, 600 bp, 700 bp, 800 bp, 900 bp, 1000 bp, 2000 bp, 3000 bp, 4000 bp or 5000 bp. In some cases, an intron may be about 300 bp. In some cases, an intron may be about 200-400 bp. In some cases, an intron may be about 100-500 bp. In some cases, an intron may be about 50-200 bp. In some cases, an intron may be either an intact naturally occurring intron or a chimeric intron. In some embodiments, the intron is located upstream of the third sequence. In some embodiments, the intron is located downstream of the promoter. In some embodiments, the second polynucleotide further comprises a regulatory element. In some embodiments, the regulatory element comprises a TPL (the tripartite leader sequence from adenovirus) and an eMLP (enhancer element from the adenovirus major late promoter) sequence. In some embodiments, the regulatory element is located upstream of the third sequence. In some embodiments, the regulatory element is located downstream of the promoter. In some embodiments, the second polynucleotide comprises a Kozak sequence. In some embodiments, the Kozak sequence is located upstream of the third sequence. In some embodiments, the Kozak sequence is located downstream of the intron. In some embodiments, the second polynucleotide comprises a human scaffold-attached region (SAR) sequence. In some embodiments, the SAR sequence is located downstream of the third sequence. In some embodiments, the SAR sequence is located upstream of the poly A signal.

In some embodiments, the second polynucleotide comprises CpG dinucleotides less than 300, 290, 280, 270, 260, 250, 240, 230, 220, 210, 200, 190, 180, 170, 160, 150, 140, 130, 120, 110, 100, 90, 80, 70, 60, 50, 40, 30, 20, or 10. In some embodiments, the second polynucleotide comprises CpG dinucleotides more than 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300. In some embodiments, the second polynucleotide comprises 100-300, 100-200, 100-150, 150-200, 150-250, 150-300, 200-250, 200-300, or 250-300 CpG dinucleotides.

In some embodiments, the second polynucleotide further comprises a fourth sequence encoding a different therapeutic protein. In some embodiments, the different therapeutic protein is a VEGF inhibitor, a PDGF inhibitor, an integrin inhibitor, an mTOR inhibitor, an angiopoietin inhibitor, or a TGFβ inhibitor.

In some embodiments, the fourth sequence and the third sequence are linked by a sequence encoding a linker. In some embodiments, the linker is a cleavable linker. In some embodiments, the cleavable linker comprises the sequence of the 2A peptide. In some embodiments, the 2A peptide may be selected from 2A peptides derived from the genus *Aphthora* or *Cardiovirus*, for example, 2A peptide of foot-and-mouth disease virus (FMDV), horse rhinitis A virus (ERAV), *Thoseaasigna* virus (TaV), or porcine teschovirus (PTV-1).

Recombinant AAV Virus Particles

In another aspect, the present disclosure provides a recombinant adeno-associated virus (rAAV) particle prepared by introducing the composition or the polynucleotide of the present disclosure into cells. In some embodiments, the cells are insect cells or mammalian cells. In some embodiments, the insect cells are Sf9 cells. In some embodiments, the cells are the mammalian cells are HEK293 cells or derivative cells thereof. In some embodiments, the derivative cells are HEK293T cells.

In some embodiments, the composition of the present disclosure can be delivered into the cell by any method known in the art. In some embodiments, the method includes but is not limited to electroporation, calcium phosphate precipitation, and liposome-mediated. In some embodiments, the composition is stably transfected into the cell. In some embodiments, the composition is transiently transfected into the cell. In some embodiments, the cells are used to produce the rAAV virus particles.

The rAAV virus particles can be isolated and purified from the cells according to methods known to those skilled in the art. For example, the rAAV can be purified using centrifugation, HPLC, hydrophobic interaction chromatography (HIC), anion exchange chromatography, cation exchange chromatography, size exclusion chromatography, ultrafiltration, gel electrophoresis, affinity chromatography, and/or other purification techniques for virus particles.

In another aspect, the present disclosure provides a rAAV particle comprising any of the polynucleotide disclosed herein.

Polynucleotide

In another aspect, the present disclosure provides a polynucleotide, comprising a codon-optimized nucleic acid sequence encoding a VEGF inhibitor. The VEGF inhibitor may be any polypeptide or protein capable of inhibiting the biological function of VEGF protein by inhibiting the activity or expression of VEGF protein. In some embodiments, the VEGF inhibitor is an anti-VEGF antibody or antigen-binding fragment thereof. In some embodiments, the antigen-binding fragments include, but are not limited to, Fab, Fab', F(ab')2, Fd, Fv, dAb, and complementarity determining region (CDR) fragments, single-chain antibodies (scFv), chimeric antibodies and diabody. In some embodiments, the anti-VEGF inhibitor is selected from ranibizumab, bevacizumab, or aflibercept.

In some embodiments, the VEGF inhibitor comprises the sequence of SEQ ID NO: 1 or a sequence having at least 70%, 80%, 90%, 95%, 96%, 97%, 98%, or 99% homology to SEQ ID NO: 1. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 1. In some embodiments, the VEGF inhibitor comprises the sequence of SEQ ID NO: 2 or a sequence having at least 70%, 80%, 90%, 95%, 96%, 97%, 98%, 99% homology to SEQ ID NO: 2. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 2. In some embodiments, the VEGF inhibitor comprises the sequence of SEQ ID NO: 3 or a sequence having at least 70%, 80%, 90%, 95%, 96%, 97%, 98%, 99% homology to SEQ ID NO: 3. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 3. In some embodiments, the VEGF inhibitor comprises the sequence of SEQ ID NO: 4 or a sequence having at least 70%, 80%, 90%, 95%, 96%, 97%, 98%, 99% homology to SEQ ID NO: 4. In some embodiments, the VEGF inhibitor comprises the sequence having at least 99.1%, 99.2%, 99.3%, 99.4%, 99.5%, 99.6%, 99.7%, 99.8% or 99.9% homology to SEQ ID NO: 4. In some embodiments, the codon-optimized nucleic acid sequence encoding a protein comprising an amino acid sequence of SEQ ID NO: 1. In some embodiments, the codon-optimized nucleic acid sequence comprises an altered number of CpG dinucleotides than SEQ ID NO: 13. In some embodiments, the codon-optimized nucleic acid sequence comprises less CpG dinucleotides than SEQ ID NO: 13. In some embodiments, the codon-optimized nucleic acid sequence comprises more CpG dinucleotides than SEQ ID NO: 13. In some embodiments, the codon-optimized nucleic acid sequence comprises less than 60, 55, 50, 45, 40, 35, 30, 25, 20, 15, 10, or 5 CpG dinucleotides. In some embodiments, the codon-optimized nucleic acid sequence comprises more than 5, 10, 15, 20, 25, 30, 35, 40, 45, 50, 55, 60, 65, 70, 75, or 80 CpG dinucleotides. In some embodiments, the codon-optimized nucleic acid sequence comprises 0-80 CpG dinucleotides. In some embodiments, the codon-optimized nucleic acid sequence comprises 5-75 CpG dinucleotides. In some embodiments, the codon-optimized nucleic acid sequence comprises 10-70 CpG dinucleotides. In some embodiments, the codon-optimized nucleic acid sequence comprises 15-65 CpG dinucleotides. In some embodiments, the codon-optimized nucleic acid sequence comprises 20-60 CpG dinucleotides. In some embodiments, the codon-optimized nucleic acid sequence comprises 25-55 CpG dinucleotides. In some embodiments, the codon-optimized nucleic acid sequence comprises 30-50 CpG dinucleotides. In some embodiments, the codon-optimized nucleic acid sequence comprises 35-45 CpG dinucleotides. In some embodiments, the codon-optimized nucleic acid sequence comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30 CpG dinucleotides. In some embodiments, the codon-optimized nucleic acid sequence does not contain CpG dinucleotides. In some embodiments, the third sequence comprises a sequence of SEQ ID NO. 14, SEQ ID NO. 15, SEQ ID NO. 16, SEQ ID NO. 17, or SEQ ID NO. 18.

In some embodiments, the polynucleotide further comprises a promoter. In some embodiments, the promoter is the CMV promoter, CAG promoter, MNDU3 promoter, PGK promoter, EF1a promoter, or an eye specific promoter. In some embodiments, the eye-specific promoter is selected from the group consisting of RPE 65 gene promoter, human retinal binding protein gene promoter, murine 11-cis retinoid alcohol dehydrogenase gene promoter, rhodopsin promoter, rhodoposin kinase promoter, tissue inhibitor of metalloproteinase 3 promoter, photoreceptor retinol binding protein promoter, vitelliform macular dystrophy 2 promoter, and interphotoreceptor retinoid-binding protein promoter.

In some embodiments, the polynucleotide further comprises other regulatory sequences, including but not limited to, inverted terminal repeats (ITR), enhancers, splicing signals, polyadenylation signals (poly A), stuffing sequences, terminators, protein degradation signals, internal ribosome entry elements (IRES), 2A sequences. In some embodiments, the poly A sequence is hGH poly(A), SV40 poly(A), or β-globin poly(A).

In some embodiments, the polynucleotide further comprises an enhancer region. In some embodiments, the enhancer region includes an SV40 enhancer, a cytomegalovirus enhancer, an IRBP enhancer, an enhancer derived from an immunoglobulin gene. In some embodiments, the enhancer region is located upstream of the CMV, CAG, MNDU3, PGK, or EF1a promoter. In some embodiments, the enhancer is located upstream of the eye-specific promoter. In some embodiments, the enhancer region is located downstream of the CMV, CAG, MNDU3, PGK, EF1a promoter. In some embodiments, the enhancer is located downstream of the eye-specific promoter.

In some embodiments, the polynucleotide further comprises an inverted terminal repeat sequence (ITR). In some embodiments, the polynucleotide comprises at least one ITR. In some embodiments, the polynucleotide comprises two ITRs. In some embodiments, the two ITRs are the same. In some embodiments, the two ITRs are different from each other. In some embodiments, the ITR is an ITR derived from AAV. In some embodiments, the ITR may be derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218 and any other known AAV. In some embodiments, the ITR has one or more base mutations, insertions, or deletions as compared to the wildtype ITR from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, AAV-218, and other known AAV, but retain the desired terminal repeat sequence functions, such as target gene replication, viruses packaging and/or integration.

In some embodiments, the polynucleotide further comprises one or more filler sequences. In some embodiments, the filler sequence is located upstream of the CMV, CAG, MNDU3, PGK, or EF1a promoter sequence. In some embodiments, the filler sequence is located downstream of the CMV, CAG, MNDU3, PGK, or EF1a promoter sequence. In some embodiments, the filler sequence is located upstream of the eye-specific promoter. In some embodiments, the filler sequence is located downstream of the eye-specific promoter. In some embodiments, the filler sequence is located at the 5' end of the 5' ITR sequence. In some embodiments, the filler sequence is located at the 3' end of the 5' ITR sequence. In some embodiments, the filler sequence is located at the 5' end of the 3' ITR sequence. In some embodiments, the filler sequence is located at the 3' end of the 3' ITR sequence.

In some embodiments, the length of the filler sequence may be about 0.1 kb-5 kb, such as but not limited to 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb or 5.0 kb.

In some embodiments, the polynucleotide further comprises an intron. In some cases, an intron may refer to any sequence that may be transcribed but is not translated. In some cases, an intron may refer to any sequence that be transcribed and is removed from a mature RNA transcript in a cell. In some cases, an intron may comprise about at least 1 bp, 50 bp, 100 bp, 150 bp, 200 bp, 300 bp, 400 bp, 500 bp, 600 bp, 700 bp, 800 bp, 900 bp, 1000 bp, 2000 bp, 3000 bp, 4000 bp or 5000 bp. In some cases, an intron may be about 300 bp. In some cases, an intron may be about 200-400 bp. In some cases, an intron may be about 100-500 bp. In some cases, an intron may be about 50-200 bp. In some cases, an intron may be either an intact naturally occurring intron or a chimeric intron. In some embodiments, the intron is located upstream of the codon-optimized nucleic acid sequence. In some embodiments, the intron is located downstream of the promoter. In some embodiments, the polynucleotide further comprises a regulatory element. In some embodiments, the regulatory element comprises a TPL (the tripartite leader sequence from adenovirus) and an eMLP (enhancer element from the adenovirus major late promoter) sequence. In some embodiments, the regulatory element is located upstream of the codon-optimized nucleic acid sequence. In some embodiments, the regulatory element is located downstream of the promoter. In some embodiments, the polynucleotide comprises a Kozak sequence. In some embodiments, the Kozak sequence is located upstream of the codon-optimized nucleic acid sequence. In some embodiments, the Kozak sequence is located downstream of the intron. In some embodiments, the polynucleotide comprises a human scaffold-attached region (SAR) sequence. In some embodiments, the SAR sequence is located downstream of the codon-optimized nucleic acid sequence. In some embodiments, the SAR sequence is located upstream of the poly A signal.

System

In another aspect, the present disclosure provides a system for treating eye diseases in a subject in need thereof, comprising the rAAV particles disclosed herein and a pharmaceutically acceptable carrier or excipient.

As used herein, "pharmaceutically or therapeutically acceptable carrier or excipient" refers to a carrier medium that does not interfere with the effectiveness of the biological activity of the active ingredient and is non-toxic to the host or patient. The type of carrier used in the pharmaceutical formulation will depend on which method of administration of the therapeutic compound is used. Methods of preparing pharmaceutical compositions for multiple routes of administration are well known in the art. "Pharmaceutically acceptable ophthalmic carrier" refers to a pharmaceutically acceptable carrier or excipient that can be used to deliver the rAAV viral particles as disclosed herein directly or indirectly to, on, or near the eye.

In some embodiments, the system is prepared by dissolving the rAAV viral particles disclosed herein in a suitable solvent. Suitable solvents include but are not limited to water, saline solutions (e.g., NaCl), buffer solutions, or other solvents. In certain embodiments, the solvent is sterile.

The aqueous solution and diluent for the suspension used in the preparation of the system may include distilled water or physiological saline. Various additives can be included. These additives may include additional ingredients, additives, or carriers suitable for contact with or use around the eyes without excessive toxicity, incompatibility, instability, irritation, allergy. Exemplary additives include solvents, bases, cosolvents, suspending agents, thickeners, emulsifiers, stabilizers, buffers, isotonicity adjusters, pH adjusters, chelating agents, soothing agents, preservatives, flavoring agents, flavoring agents, colorants, excipients, binders, lubricants, surfactants, absorption enhancers, dispersants, preservatives, and solubilizers.

For example, a buffer is added to keep the pH constant, and the buffer may include a pharmaceutically acceptable buffer, such as borate buffer, citrate buffer, tartrate buffer, phosphate buffer, acetate buffer or Tris-HCl buffer (containing tris (hydroxymethyl)aminomethane and HCl).

In addition to the buffer, an isotonic agent may be added to the system to prepare a preparation that is isotonic with tears. Isotonic agents include, but are not limited to sugars, such as dextrose, glucose, sucrose, and fructose; sugar alcohols, such as mannitol and sorbitol; polyols, such as glycerin, polyethylene glycol, and propylene glycol; and salts, such as chlorinated sodium, sodium citrate, benzalkonium chloride, phedrine chloride, potassium chloride, procaine chloride, chloram phenicol and sodium succinate. An isotonic agent is added in such an amount that the osmotic pressure of the eye drops is equal to the osmotic pressure of tears.

In some embodiments, it is also desirable to use additional agents, including but not limited to, stabilizers, such as sodium sulfite, sodium carbonate, and propylene glycol; antioxidants, such as ascorbic acid, sodium ascorbate, butylated hydroxytoluene (BHT), butylated hydroxyanisole (BHA), tocopherol, sodium thiosulfate; and/or chelating agents, such as ethylenediaminetetraacetic acid (EDTA), ethylene glycol-bis-(2-aminoethyl)-N, N,N,N-tetraacetic acid (EGTA) and sodium citrate.

The system disclosed herein can be prepared by aseptic procedures, or alternatively can be sterilized at a suitable stage of preparation. For example, the system can be prepared by aseptically mixing sterile ingredients. Alternatively, the system can be prepared by first mixing the ingredients and then sterilizing the final formulation. Sterilization methods can include, but are not limited to heat sterilization, radiation, and filtration.

The rAAV virus particles disclosed herein can also be provided in combination with other therapeutic agents. In various embodiments, the compounds disclosed herein may also be provided in combination with an ocular therapeutic agent selected from the group consisting of Acular® (ketoprofen tromethamine ophthalmic solution) 0.5%, Acuvail® (ketorolac tromethamine), AK-Con-A® (naphazoline eye drops), Akten® (lidocaine hydrochloride), Alamast® (pemirolast potassium), Alphagan® (bromidine), Alrex® (loteprednol etabonate), Astepro® (Azelastine hydrochloric acid), AzaSite® (azithromycin), Bepreve® (bepotastine besylate ophthalmic solution), Besivance® (besifloxacin ophthalmic suspension), Betaxon® (levobetaxolol hydrochloride), BSS sterile lavage solution, Cosopt® (dorzolamide/timolol), Durezol® (difluprednate), Eylea® (Aflibercept), Lotemax℠, Lucentis® (ranibizumab), Lumigan® (bimatoprost ophthalmic solution), Macugen® (pegaptanib), Ocuflox® (ofloxacin 0.3%), OcuHist® (naphazoline hcl/pheniramine), Ozurdex® (dexamethasone), Quixin® (levofloxacin), Rescula® (unoprostone isopropyl ophthalmic solution) 0.15%, Restasis® (cyclosporin ophthalmic emulsion), Salagen® (pilocarpine) tablets, Travatan® (travoprost ophthalmic solution), Valcyte® (valganciclovir hydrochloride), trifluorothymidine (Viroptic®), Vistide® (cidofovir), Visudyne® (verteporfin for injection), Vitrasert® (ganciclovir) implants, formamivir injection, ZADITOR® (ketotifen 0.025%), Zioptan® (tafluprost ophthalmic solution), Zirgan® (ganciclovir ophthalmic gel), Zymaxid® (gatifloxacin ophthalmic solution), atropine, Flurbiprofen, Physostigmine, Azopt® (brinzolamide 1%), Gentamicin, Proparacaine, Bacitracin, Goniosol® (Hypromellose Eye Drops), Polymyxin B, Betadine® (Povidone iodine), gramicidin, prednisolone, Humorsol®, promethaine, Betoptic® (betaxolol eye drops), Hylartin® (sodium hyaluronate injection), Propine®, brinzolamide, Hypertonic NaCl, Puralube®, Indocycanine Green, Rose Bengal, Itraconazole, Sodium Hyaluronate, Cefazolin, Xalatan® (Latanoprost), Sulofen, Xiao Celluvisc®, mannitol, oxytetracycline, chloramphenicol, methazolamide, timolol, Ciloxan, miconazole, tobramycin, ciprofloxacin, Miostat® (carbachol), triamcinolone, Muro 128®, Demecarium, neomycin, Topamax® (topiramate), Neptazane, Trusopt® (Dorzolamide), Dipicolin, adenosine arabinoside, Vira-A®, epinephrine, trifluorothymidine, fluorescence, and phenylephrine.

Exemplary drugs may include anti-angiogenic agents, such as angiostatin, anecotastat, thrombospondin, VEGF receptor tyrosine kinase inhibitors; anti-vascular endothelial growth factor (anti-VEGF) drugs, such as ranibizumab, bevacizumab, pegaptanib, sunitinib, sorafenib, and any other known small molecules and transcription inhibitors for angiogenesis; ophthalmic drugs, including glaucoma agents, such as adrenergic antagonists (e.g., beta-blockers such as acetbutolol, atenolol, bisoprolol, carvedilol, asmolol, labetalol, nadolol, penbutolol, pindolol, propranolol, metipranolol, betaxolol, carteolol, levobetaxolol, levobunolol and timolol; adrenergic agonists or sympathomimetics, such as epinephrine, dipivefrin, clonidine, aparclonidine, and brimonidine; parasympathomimetics or cholinergic receptor agonists, such as pilocarpine, carbachol, phospholine iodine, physostigmine, salicylic acid, acetylcholine chloride, eserine, diisopropylfluorophosphate, demecariumbromide; muscarinic; carbonic anhydrase inhibitors agents, including local and/or systemic agents, such as acetozolamide, brinzolamide, dorzolamide, methazolamide, ethoxzolamide, diamox, and dichlorphenamide; mydriatic-cycloplegic agents, such as atropine, cyclopentolate, succinylcholine, homatropine, phenylephrine, scopolamine, and tropicamide; prostaglandins, such as prostaglandin F2α, antiprostaglandin, prostaglandin precursor; or prostaglandin analogue agents, such as bimatoprost, latanoprost, travoprost and unoprostone.

Additional exemplary drugs may also include anti-inflammatory drugs, including, for example, glucocorticoids and corticosteroids such as betamethasone, cortisone, dexamethasone, dexamethasone 21-phosphate, methylprednisolone, prednisolone 21-phosphate, prednisolone acetate, prednisolone, flumiron, loteprednol, methylprednisolone, fluocinolone, triamcinolone, triamcinolone, triamcinolone acetate, beclomethasone, budesonide, flunisolide, flumethasone, fluticasone, fludrocortisone, hydrocortisone, hydrocortisone acetate, loteprednol, rimetholone; nonsteroidal anti-inflammatory drugs, including, aspirin, diclofenac, flurbiprofen, ibuprofen, bromfenac, nepafenac, ketoprofen, salicylates, indomethacin, naxopren, piroxicam,nabumetone diflunisal, etodolac, fenoprofen, flurbiprofen, indomethacin, ketoprofen, chlorate, mefenamic acid, meloxicam, nabumetone, oxaprozin, piroxicam, disalicylate, sulindac and tolmetin; COX-2 inhibitors, such as celecoxib, rofecoxib, and valdecoxib; anti-infection or antimicrobial agents, such as antibiotics, for example, tetracycline, chlortetracycline, bacitracin, neomycin, polymyxin, brevibacillin, cephalexin, oxytetracycline, chloramphenicol, rifampicin, ciprofloxacin, tobramycin, gentamicin, erythromycin, penicillin, sulfonamides, sulfadiazine, sulfacetamide, sulfamethoxazole, sulfisoxazole, nitrofurazone, sodium propionate, aminoglycosides such as gentamicin, tobramycin, amikacin and streptomycin; fluoroquinolones, such as ciprofloxacin, gatifloxacin, levofloxacin, moxifloxacin, norfloxacin, ofloxacin; bacitracin, erythromycin, fusidic acid, neomycin, polymyxin B, gramicidin, alpha oxybenzidine and sulfamethoxamide; antifungal agents, such as amphotericin B, caspofungin, clotrimazole, fluconazole, itraconazole, ketoconazole, voriconazole, terbinafine, nystatin and miconazole; antimalarial agents, such as chloroquine, atovaquone, mefloquine, primaquine, quinidine and quinine; antimycobacterial agents, such as ethambutol, isoniazid, pyrazinamide, rifampin and Rifabutin; antiparasitic agents, such as albendazole, mebendazole, thiobendazole, bisazolate suppository, thiuracil, atovaquone, iodoquinaol, ivermectin, paromomycin, praziquantel, and trimatrexate.

Methods

In another aspect, the present disclosure provides a method for expressing a VEGF inhibitor in a cell or a tissue of a subject, comprising administering to the cell or the tissue of the subject any of the compositions, rAAV particles, polynucleotides, or systems disclosed herein. In some embodiments, the composition, rAAV particle, polynucleotide, or system may be administered to the subject by any suitable method known in the art. In some embodiments, the cell or the tissue is eye related. In some embodiments, the composition, rAAV particle, polynucleotide, or system can be applied to the eye by subconjunctival, retrobulbar, periocular, subretinal, suprachoroidal, or intraocular route.

In another aspect, the present disclosure provides a method for treating ocular diseases, which comprises administering a therapeutically effective amount of the composition, rAAV particle, polynucleotide, or system disclosed herein to a subject in need.

In some embodiments, the system may be administered to the subject by any suitable method known in the art. In some embodiments, the system can be applied to the eye by subconjunctival, retrobulbar, periocular, subretinal, suprachoroidal, or intraocular route.

In some embodiments, the ocular diseases include, but are not limited to, age-related macular degeneration (AMD), wet AMD, dry AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, and diabetic retinal edema.

In some embodiments, the system comprising the rAAV viral particles is provided in a therapeutically effective amount that achieves the desired biological effect at a medically acceptable level of toxicity. The dosage may vary based on the route of administration and the severity of the disease. The dose may also be adjusted according to the weight, age, sex and/or degree of symptoms of each patient to be treated. It is understood that routine changes in dosage may need to be made according to the age and weight of the patient and the severity of the condition to be treated.

In some embodiments, the therapeutically effective amount is generally about $1\times10^5$-$1\times10^{13}$ rAAV virus particles. In some embodiments, the therapeutically effective amount is generally about $1\times10^6$ $1\times10^{12}$ rAAV virus particles. In some embodiments, the therapeutically effective amount is generally about $1\times10^7$-$1\times10^{12}$ rAAV virus particles. In some embodiments, the therapeutically effective amount is generally about $1\times10^8$-$1\times10^{12}$ rAAV virus particles. In some embodiments, the therapeutically effective amount is generally about $1\times10^9$-$1\times10^{12}$ rAAV virus particles. In some embodiments, the therapeutically effective amount is generally about $1\times10^{10}$-$1\times10^{12}$ rAAV virus particles.

In some embodiments, the volume delivered is about 0.005 mL-0.5 mL per eye. In some embodiments, the volume delivered is about 0.05 mL-0.5 mL per eye. In some embodiments, the volume delivered is about 0.1 mL-0.5 mL per eye. In some embodiments, the volume delivered is about 0.2 mL-0.5 mL per eye.

In some embodiments, the frequency of administration may be at least once a day, including 2, 3, 4, or 5 times a day. In some embodiments, the treatment can last for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days Days, 48 days, 49 days, 50 days, 60 days, 70 days, 80 days, 90 days, 100 days, 150 days, 200 days, 250 days, 300 days, 400 days, 500 days, 750 days, 1000 days or More than 1000 days.

In some embodiments, administration of the rAAV particles or the polynucleotides can also include ex vivo administration. In some embodiments, the ex vivo administration comprises (1) isolation of cells or tissue(s) of interest from a subject, (2) contacting the cells or tissue(s) with rAAVs in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection. In some embodiments, the cells or tissues are eye related.

In another aspect, the present disclosure provides a method for preparing a recombinant adeno-associated virus (rAAV) particle, comprising transfecting a cell with any of the compositions, rAAV particles, polynucleotides, or systems disclosed herein. In some embodiments, the cell is an insect cell or a mammalian cell. In some embodiments, the insect cell is the Sf9 cell. In some embodiments, the mammalian cell is the HEK293 cell or a derivative cell thereof. In some embodiments, the derivative cell is the HEK293T cell. In some embodiments, the method comprises generating bacmid DNA and/or baculovirus. In some embodiments, the method comprises generating bacmid DNA comprising the VEGF inhibitor expression sequence (such as the polynucleotides disclosed herein). In some embodiments, the method comprises generating bacmid DNA rAAV cap-rep expression sequence. In some embodiments, the method comprises transfecting a cell with the bacmid DNA to produce baculoviruses. In some embodiments, the method comprises transfecting a cell with the bacmid DNA comprising the VEGF inhibitor expression sequence to produce baculoviruses. In some embodiments, the method comprises transfecting a cell with the bacmid DNA to produce baculoviruses comprising the rAAV cap-rep expression sequence. In some embodiments, the method further comprises mixing the baculoviruses to infect a cell (such as the Sf9 cell) to obtain packaged rAAV/VEGF inhibitor virus particles disclosed herein.

In some embodiments, the compositions disclosed herein or the polynucleotides disclosed herein can be delivered into the cell by any method known in the art. In some embodiments, the method includes but is not limited to electroporation, calcium phosphate precipitation, and liposome-mediated. In some embodiments, the composition or the polynucleotide is stably transfected into the cell. In some embodiments, the composition or the polynucleotide is transiently transfected into the cell. Delivery vehicles such as liposomes, nanocapsules, microparticles, microspheres, lipid particles, vesicles, and the like, may be used for the introduction of the vectors, the compositions, or the polynucleotides into the cells. In particular, the vectors, the compositions, or the polynucleotides may be formulated for delivery either encapsulated in a lipid particle, a liposome, a vesicle, a nanosphere, or a nanoparticle.

Kits

On the other hand, the present disclosure provides a kit for treating eye diseases, which comprises the rAAV particle or the system disclosed herein and instructions. In some embodiments, the instructions are used to indicate a method of administering the rAAV particle or the system to treat ocular diseases.

In some embodiments, the kit further comprises a container. In some embodiments, the container is configured to deliver the system described herein. In some embodiments, the container includes a vial, dropper, bottle, tube, and syringe. In some embodiments, the container is a dropper for applying the system. In some embodiments, the container is a syringe for administering the system.

Some embodiments of the present disclosure are further illustrated by the following examples, which should not be construed as limiting. Those skilled in the art will understand that the technology disclosed in the following examples represents a technique that the inventors have found to work well in the implementation of the embodiments described herein, and therefore can be considered to constitute what is used to implement these embodiments. However, based on the present disclosure, those skilled in the art will understand that many changes can be made in the specific embodiments disclosed herein without departing from the spirit and scope of the present invention, and the same or similar results can still be obtained.

EXAMPLES

The following examples further illustrate the invention. These examples are only intended to illustrate the present invention and should not be construed as limiting the present invention.

Example 1 Design of Recombinant AAV Vector

The cap and rep coding sequences derived from AAV2 together with their corresponding promoters were synthesized and cloned into pUC57, pFastBac1, modified pUC57, or modified pFastBac1 to obtain the first polynucleotide comprising the coding sequences of cap and rep proteins.

The nucleotide sequence encoding the green fluorescent protein (GFP) or the nucleic acid sequence encoding the VEGF inhibitor aflibercept were synthesized and cloned into pUC57, pFastBac1, modified pUC57, or modified pFastBac1 with their corresponding promoters to obtain a second polynucleotide containing coding sequences of GFP or Aflibercept, respectively. The design of the contruct for the second polynucleotide can be found in Table 2.

TABLE 2

| Construct Design | |
|---|---|
| Construct No. | Construct Design |
| 1 | CMVep-TPL-eMLP-Aflibercept-co1-SAR-hGHpA |
| 2 | CAG-Aflibercept-co1-SV40pA |
| 3 | CAG-Aflibercept-co1-rbGlobpA |
| 4 | MND-Aflibercept-co1-SV40pA |

TABLE 2-continued

| Construct Design | |
|---|---|
| Construct No. | Construct Design |
| 5 | CMVep-TPL-eMLP-Aflibercept-co2-SAR-hGHpA |
| 6 | CAG-Aflibercept-co2-SV40pA |
| 7 | CAG-Aflibercept-co2-rbGlobpA |
| 8 | MND-Aflibercept-co2-SV40pA |
| 9 | CMVep-TPL-eMLP-Aflibercept-co3-SAR-hGHpA |
| 10 | CAG-Aflibercept-co3-SV40pA |
| 11 | CAG-Aflibercept-co3-rbGlobpA |
| 12 | MND-Aflibercept-co3-SV40pA |
| 13 | CMVep-TPL-eMLP-GFP-SAR-hGHpA-Stuffer |
| 14 | CAG-GFP-SV40pA-Stuffer |
| 15 | CAG-GFP-rbGlobpA-Stuffer |
| 16 | MND-GFP-sv40pA-Stuffer |
| 17 | MND-sv40i-Aflibercept-co1-sv40pA |
| 18 | MND-sv40i-Aflibercept-co1-sv40pA (scAAV) |
| 19 | MND-sv40i-GFP-sv40pA-Stuffer |
| 20 | MND-sv40i-GFP-sv40pA-Stuffer (scAAV) |

"co" refers to "codon optimized." For example, "co1" refers to codon-optimized sequence #1. "CMVep" refers to CMV enhancer and promoter. "sv40i" refers to SV40 intron.

Example 2 Plasmid Transfection

Figure 1B:
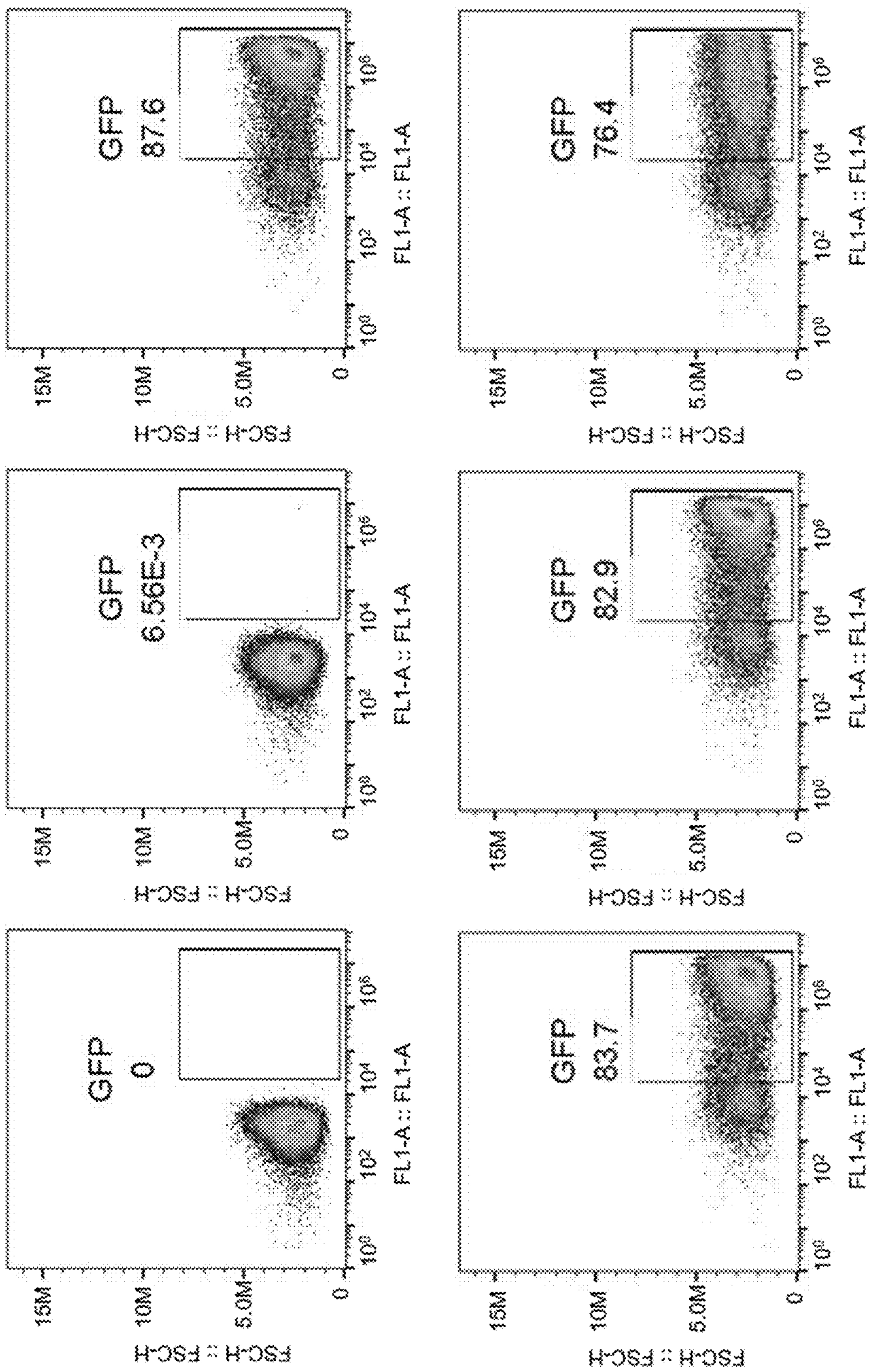
FIG. 1B illustrates the Flow Cytometry result showing the percentage of GFP expressing cells 48 hours after transfection.

To determine the expression intensity of designed constructs, $2\times10^5$ HEK293T cells were seeded in a 24-well plate and cultured overnight. 0.5 μg of each expression construct plasmid was mixed with 1.5 μL Mirus TransiT-VirusGEN® Transfection Reagent per well in 50 μL Opti-Mem medium (DNA (ug): Mirus reagent (ul)=1:3). After 48 hours, the expression of GFP was detected by a fluorescent microscope and a flow cytometer (FIGS. 1A and 1B), suggesting that the cells were successfully transfected with the expression cassette. The supernatant culture medium was harvested 48 hours later for aflibercept detection.

Example 3 Preparation of Recombinant AAV Virus Particles

The first polynucleotide and the second polynucleotide obtained in Example 1 were mixed to form a composition, and the composition plus a helper plasmid were used to transfect HEK293T cells to obtain packaged rAAV2.7m8/Aflibercept virus particles and rAAV2.7m8/GFP virus particles. The AAV particles could also be produced by the bac to AAV technology, i.e., first generate two bacmids containing Rep-Cap and transgene expression cassette, respectively, then produce baculoviruses for these two bacmids, the rAAV could be produced by infecting both Rep-Cap and transgene expression baculoviruses in Sf9 cells. The recombinant AAV2.7m8/Aflibercept virus particles and AAV2.7m8/GFP virus particles were isolated and purified from the HEK293T cells using gradient ultracentrifugation.

Example 4 Expression Levels of Aflibercept from the Transfected Cells

The expression levels of Aflibercept in cell culture supernatant were measured by a quantitative ELISA. ELISA plates were coated with 100 uL/well of recombinant human VEGFA (rh VEGFA) at a concentration of 1 ug/mL in coating buffer and incubated overnight at 4° C. After washing with wash buffer, the plates were blocked with 300 uL/well of protein-free blocking buffer. Afterward, the plates were washed, and the samples were added (100 uL/well) at 1:1000 dilution and incubated for 2 hr at room temperature. The plates were then washed again, and 100 uL/well of anti-human Fc domain of IgG (Fcγ)-specific antibody conjugated to horseradish peroxidase (HRP) at 500 ng/ml in BSA 1% in PBS was added to the wells. After washing, 100 uL/well of SuperSignal ELISA Pico Chemiluminescent Substrate was added to the wells, and luminescence signal was measured using a microplate reader. The result is shown in Table 3.

TABLE 3

ELISA Data

| Construct No. | Construct Design | Aflibercept concentration (ng/ml) n = 3 |
|---|---|---|
| 1 | CMVep-TPL-eMLP-Aflibercept-co1-SAR-hGHpA | A |
| 2 | CAG-Aflibercept-co1-SV40pA | B |
| 3 | CAG-Aflibercept-co1-rbGlobpA | A |
| 4 | MND-Aflibercept-co1-SV40pA | C |
| 5 | CMVep-TPL-eMLP-Aflibercept-co2-SAR-hGHpA | B |
| 6 | CAG-Aflibercept-co2-SV40pA | C |
| 7 | CAG-Aflibercept-co2-rbGlobpA | B |
| 8 | MND-Aflibercept-co2-SV40pA | C |
| 9 | CMVep-TPL-eMLP-Aflibercept-co3-SAR-hGHpA | A |
| 10 | CAG-Aflibercept-co3-SV40pA | B |
| 11 | CAG-Aflibercept-co3-rbGlobpA | A |
| 12 | MND-Aflibercept-co3-SV40pA | C |
| 13 | CMVep-TPL-eMLP-GFP-SAR-hGHpA-Stuffer | D |
| 14 | CAG-GFP-SV40pA-Stuffer | D |
| 15 | CAG-GFP-rbGlobpA-Stuffer | D |
| 16 | MND-GFP-sv40pA-Stuffer | D |
| 17 | MND-sv40i-Aflibercept-co1-sv40pA | C |
| 18 | MND-sv40i-Aflibercept-co1-sv40pA (different ITRs) | C |
| 19 | MND-sv40i-GFP-sv40pA-Stuffer | D |
| 20 | MND-sv40i-GFP-sv40pA-Stuffer (scAAV) | D |

Data are designed within the following ranges: Aflibercept concentration (ng/ml): A > 15,000 > B > 10,000 > C > 1000 > D

Example 5. Activity Level of Alibercept from rAAV

HUVEC Proliferation Assay was utilized to measure the activity level of aflibercept expressed after rAAV transduction in 293T cells. Particularly, 100 μl human umbilical vein endothelial cells (HUVECs) suspension was dispensed in basal medium (about 5000 cells/well) in a 96-well plate. The plate was incubated for 4 hours. 100× dilution of supernatant samples were prepared with VEGF (80 ng/mL) in basal medium and incubated for 1 hours. 100 μl of dilution was added into the HUVECs. The plate was incubated for 4 days. 20 μl of cell counting kit-8 (CCK-8) solution was added to each well of the plate. The plate was incubated for 4 hours in the incubator. The plate was read at 450 nm.

The inhibitory activity of aflibercept on the HUVECs was calculated based on the following equation:

$$\text{Inhibition }\%=(OD_{(GFP\ control)}-OD_{(sample)})/(OD_{(GFP\ control)}-OD_{(blank)})*100\%$$

As appreciated by a person skilled in the art, CCK-8, being nonradioactive, allows sensitive colorimetric assays for the determination of the number of viable cells in cell proliferation and cytotoxicity assays. WST-8 is reduced by dehydrogenases in cells to give an orange colored product (formazan), which is soluble in the tissue culture medium. The amount of formazan produced is directly proportional to the number of living cells and is measured by absorbance at 460 nm. Cell Counting Kit 8 (WST-8/CCK8) (ab228554) provides a convenient and robust way of performing a cell viability assay. The kit uses a water-soluble tetrazolium salt to quantify the number of live cells by producing an orange formazan dye upon bio-reduction in the presence of an electron carrier.

The result showed that secreted aflibercept inhibited VEGF-induced HUVEC proliferation. In other words, the secreted aflibercept retained the biologically activity. The result is shown in Table 4.

TABLE 4

HUVEC Proliferation Assay Data

| Construct No. | Construct Design | Inhibition of HUVEC cell proliferation, n = 9 |
|---|---|---|
| 1 | CMVep-TPL-eMLP-Aflibercept-co1-SAR-hGHpA | A |
| 2 | CAG-Aflibercept-co1-SV40pA | B |
| 3 | CAG-Aflibercept-co1-rbGlobpA | A |
| 4 | MND-Aflibercept-co1-SV40pA | D |
| 5 | CMVep-TPL-eMLP-Aflibercept-co2-SAR-hGHpA | A |
| 6 | CAG-Aflibercept-co2-SV40pA | B |
| 7 | CAG-Aflibercept-co2-rbGlobpA | B |
| 8 | MND-Aflibercept-co2-SV40pA | D |
| 9 | CMVep-TPL-eMLP-Aflibercept-co3-SAR-hGHpA | A |
| 10 | CAG-Aflibercept-co3-SV40pA | A |
| 11 | CAG-Aflibercept-co3-rbGlobpA | A |
| 12 | MND-Aflibercept-co3-SV40pA | D |
| 13 | CMVep-TPL-eMLP-GFP-SAR-hGHpA-Stuffer | D |
| 14 | CAG-GFP-SV40pA-Stuffer | D |
| 15 | CAG-GFP-rbGlobpA-Stuffer | D |
| 16 | MND-GFP-sv40pA-Stuffer | D |
| 17 | MND-sv40i-Aflibercept-co1-sv40pA | B |
| 18 | MND-sv40i-Aflibercept-co1-sv40pA (scAAV) | B |
| 19 | MND-sv40i-GFP-sv40pA-Stuffer | D |
| 20 | MND-sv40i-GFP-sv40pA-Stuffer (scAAV) | D |

Data are designed within the following ranges: Inhibition of HUVEC cell proliferation: A > 40 > B > 25 > C > 10 > D

Example 6. In Vitro AAV Infection 100 uL of $6\times10^5$ cells/mL 293T cells ($6\times10^4$/well) were seeded in DMEM complete medium each well in a 96-well plate. The cells were cultured for 1 hour and then the medium was discarded. 30 uL DMEM complete medium with 7m8 AAV vectors at MOI $5.56\times10^3$ and 1.67 × 104 was added to each well and incubated overnight. The MOIs were calculated based on droplet digital PCR (ddPCR) titers. Next day, 70 uL DMEM complete medium was added. The cells were cultured for 48 hours in total.

Next, the expression levels of Aflibercept in cell culture supernatant were measured by a quantitative ELISA. ELISA plates were coated with 100 uL/well of recombinant human VEGFA (rh VEGFA) at a concentration of 1 ug/mL in coating buffer and incubated overnight at 4° C. After washing with wash buffer, the plates were blocked with 300 uL/well of protein-free blocking buffer. Afterward, the plates were washed, and the samples were added (100 uL/well) at 1:1000 dilution and incubated for 2 hr at room temperature. The plates were then washed again, and 100 uL/well of anti-human Fc domain of IgG (Fcγ)-specific antibody conjugated to horseradish peroxidase (HRP) at 500 ng/ml in BSA 1% in PBS was added to the wells. After washing, 100 uL/well of SuperSignal ELISA Pico Chemiluminescent Substrate was added to the wells, and luminescence signal was measured using a microplate reader. The result is shown in Table 5.

TABLE 5

Aflibercept ELISA data

| Construct No. | Construct Design | Aflibercept concentration (ng/ml) n = 4, MOI = 1.67E+4 | Aflibercept concentration (ng/ml) n = 4, MOI = 5.56E+3 |
|---|---|---|---|
| 1 | CMVep-TPL-eMLP-Aflibercept-co1-SAR-hGHpA | A | A |
| 2 | CAG-Aflibercept-co1-SV40pA | B | C |
| 3 | CAG-Aflibercept-co1-rbGlobpA | A | A |
| 9 | CMVep-TPL-eMLP-Aflibercept-co3-SAR-hGHpA | A | A |
| 10 | CAG-Aflibercept-co3-SV40pA | D | C |
| 11 | CAG-Aflibercept-co3-rbGlobpA | A | A |
| 15 | CAG-GFP-rbGlobpA-Stuffer | D | D |
| 17 | MND-sv40i-Aflibercept-co1-sv40pA | A | C |
| 18 | MND-sv40i-Aflibercept-co1-sv40pA (scAAV) | A | C |

Data are designed within the following ranges: for the left column (MOI = 1.67E+4), Aflibercept concentration (ng/ml): A > 3,000 > B > 2,000 > C > 1,000 > D; for the right column (MOI = 5.56E+3), Aflibercept concentration (ng/ml): A > 1,500 > B > 1,000 > C > 500 > D.

Example 7. Measurement of the Activity of Aflibercept from rAAV 20 uL of aflibercept supernatant samples were mixed with 20 uL DMEM complete medium (containing 2 ug/mL VEGF) and incubated for 1 hour. 25 uL of the sample dilutions was dispensed to the 25 uL of preplated cells according to the manufacture's instruction of VEGF Bioassay (Promega GA2001). The activity of Aflibercept is calculated based on the following equation:

Fold Inhibition=RLU (cells only−assay sample)/RLU (cells only-background)

(RLU: Relative Light Units)

The result of the inhibition of VEGF by aflibercept expressed from rAAV suggested that the secreted aflibercept in the culture supernatant is biologically active. The data is shown in Table 6.

| Construct No. | Construct Design | Inhibition of VEGF (Luciferase-reporter) n = 4, MOI = 1.67E+4 | Inhibition of VEGF (Luciferase-reporter) n = 4, MOI = 5.56E+3 |
|---|---|---|---|
| 1 | CMVep-TPL-eMLP-Aflibercept-co1-SAR-hGHpA | A | A |
| 2 | CAG-Aflibercept-col-SV40pA | C | D |
| 3 | CAG-Aflibercept-col-rbGlobpA | A | A |
| 9 | CMVep-TPL-eMLP-Aflibercept-co3-SAR-hGHpA | A | B |
| 10 | CAG-Aflibercept-co3-SV40pA | C | D |
| 11 | CAG-Aflibercept-co3-rbGlobpA | A | D |
| 15 | CAG-GFP-rbGlobpA-Stuffer | D | D |
| 17 | MND-sv40i-Aflibercept-co1-sv40pA | D | D |
| 18 | MND-sv40i-Aflibercept-co1-sv40pA (scAAV) | D | D |

Data are designed within the following ranges:

for the left column (MOI=1.67E+4), inhibition of VEGF (Luciferase-reporter): A>60>B>40>C>20>D; for the right column (MOI=5.56E+3), inhibition of VEGF (Luciferase-reporter): A>35>B>25>C>15>D.

Example 8 Delivery and Expression of VEGF Inhibitor in Mice

The mice are divided into two groups: the control group and the experimental group. The mice in both groups are injected intravitreally with the virus particles of AAV2.7m8/VEGF inhibitor purified in Example 3, respectively. The eye tissues are collected to measurement concentration of aflibercept by ELISA.

Example 9 the Efficacy of the Composition of the Present Application In Vivo

Laser-induced choroidal neovascularization (LCNV) is a model of choroidal angiogenesis that is used as a preclinical model of wet age-related macular degeneration. A 2-arm clinical experiment is conducted using a control, system containing rAAV2.7m8/VEGF inhibitor virus particles in this application to verify the effectiveness of the system described in this application.

List of Sequences amino acid sequence of Aflibercept

SEQ ID NO: 1

SDTGRPFVEMYSEIPEIIHMTEGRELVIPCRVTSPNITVTLK

KFPLDTLIPDGKRIIWDSRKGFIISNATYKEIGLLTCEATVN

GHLYKTNYLTHRQTNTIIDVVLSPSHGIELSVGEKLVLNCTA

RTELNVGIDFNWEYPSSKHQHKKLVNRDLKTQSGSEMKKFLS

TLTIDGVTRSDQGLYTCAASSGLMTKKNSTFVRVHEKDKTHT

CPPCPAPELLGGPSVFLFPPKPKDTLMISRTPEVTCVVVDVS

HEDPEVKFNWYVDGVEVHNAKTKPREEQYNSTYRVVSVLTVL

HQDWLNGKEYKCKVSNKALPAPIEKTISKAKGQPREPQVYTL

PPSRDELTKNQVSLTCLVKGFYPSDIAVEWESNGQPENNYKT

TPPVLDSDGSFFLYSKLTVDKSRWQQGNVFSCSVMHEALHNH

YTQKSLSLSPG

-continued amino acid sequence of VEGF Receptor 1 (VEGFR1) domain 2-VEGF Receptor 2 (VEGFR2) domain 3 fusion protein

SEQ ID NO: 2

SDTGRPFVEMYSEIPEIIHMTEGRELVIPCRVTSPNITVTLK

KFPLDTLIPDGKRIIWDSRKGFIISNATYKEIGLLTCEATVN

GHLYKTNYLTHRQTNTIIDVVLSPSHGIELSVGEKLVLNCTA

RTELNVGIDFNWEYPSSKHQHKKLVNRDLKTQSGSEMKKFLS

TLTIDGVTRSDQGLYTCAASSGLMTKKNSTFVRVHEDPIEGR amino acid sequence of VEGF Receptor 1 (VEGFR1) domain 2

SEQ ID NO: 3

SDTGRPFVEMYSEIPEIIHMTEGRELVIPCRVTSPNITVTLK

KFPLDTLIPDGKRIIWDSRKGFIISNATYKEIGLLTCEATVN

GHLYKTNYLTHRQTNTIID amino acid sequence of VEGF Receptor 2 (VEGFR2) domain 3

SEQ ID NO: 4

VVLSPSHGIELSVGEKLVLNCTARTELNVGIDFNWEYPSSKH

QHKKLVNRDLKTQSGSEMKKFLST LTIDGVTRSDQGLYTCA

ASSGLMTKKNSTFVRVHEDPIEGR amino acid sequence of CDR1 of heavy chain

SEQ ID NO: 5

GYDFTHYGMN amino acid sequence of CDR2 of heavy chain

SEQ ID NO: 6

WINTYTGEPTYAADFKR amino acid sequence of CDR3 of heavy chain

SEQ ID NO: 7

YPYYYGTSHWYFDV amino acid sequence of CDR1 of light chain

SEQ ID NO: 8

SASQDISNYLN amino acid sequence of CDR1 of light chain

SEQ ID NO: 9

FTSSLHS amino acid sequence of CDR2 of light chain

SEQ ID NO: 10

QQYSTVPWT amino acid sequence of variable domain of heavy chain (VH)

SEQ ID NO: 11

EVQLVESGGGLVQPGGSLRLSCAASGYDFTHYGMNWVRQAPG

KGLEWVGWINTYTGEPTYAADFKRRFTFSLDTSKSTAYLQMN

SLRAEDTAVYYCAKYPYYYGTSHWYFDVWGQGTLVTVSSAST

KGPSVFPLAPSSKSTSGGTAALGCLVKDYFPEPVTVSWNSGA

LTSGVHTFPAVLQSSGLYSLSSVVTVPSSSLGTQTYICNVNH

KPSNTKVDKKVEPKSCDKTHL

-continued amino acid sequence of variable domain of light chain (VL)

SEQ ID NO: 12

DIQLTQSPSSLSASVGDRVTITCSASQDISNYLNWYQQKPGK

APKVLIYFTSSLHSGVPSRFSGSGSGTDFTLTISSLQPEDFA

TYYCQQYSTVPWTFGQGTKVEIKRTVAAPSVFIFPPSDEQLK

SGTASVVCLLNNFYPREAKVQWKVDNALQSGNSQESVTEQDS

KDSTYSLSSTLTLSKADYEKHKVYACEVTHQGLSSPVTKSFN

RGEC

VEGF-trap (aflibercept) nucleic acid sequence (WO2005000895)

SEQ ID NO: 13

ATGGTCAGCTACTGGGACACCGGGGTCCTGCTGTGCGCGCTG

CTCAGCTGTCTGCTTCTCACAGGATCTAGTTCCGGAAGTGAT

ACCGGTAGACCTTTCGTAGAGATGTACAGTGAAATCCCCGAA

ATTATACACATGACTGAAGGAAGGGAGCTCGTCATTCCCTGC

CGGGTTACGTCACCTAACATCACTGTTACTTTAAAAAAGTTT

CCACTTGACACTTTGATCCCTGATGGAAAACGCATAATCTGG

GACAGTAGAAAGGGCTTCATCATATCAAATGCAACGTACAAA

GAAATAGGGCTTCTGACCTGTGAAGCAACAGTCAATGGGCAT

TTGTATAAGACAAACTATCTCACACATCGACAAACCAATACA

ATCATAGATGTGGTTCTGAGTCCGTCTCATGGAATTGAACTA

TCTGTTGGAGAAAAGCTTGTCTTAAATTGTACAGCAAGAACT

GAACTAAATGTGGGGATTGACTTCAACTGGGAATACCCTTCT

TCGAAGCATCAGCATAAGAAACTTGTAAACCGAGACCTAAAA

ACCCAGTCTGGGAGTGAGATGAAGAAATTTTTGAGCACCTTA

ACTATAGATGGTGTAACCCGGAGTGACCAAGGATTGTACACC

TGTGCAGCATCCAGTGGGCTGATGACCAAGAAGAACAGCACA

TTTGTCAGGGTCCATGAAAAGGACAAAACTCACACATGCCCA

CCGTGCCCAGCACCTGAACTCCTGGGGGGACCGTCAGTCTTC

CTCTTCCCCCCAAAACCCAAGGACACCCTCATGATCTCCCGG

ACCCCTGAGGTCACATGCGTGGTGGTGGACGTGAGCCACGAA

GACCCTGAGGTCAAGTTCAACTGGTACGTGGACGGCGTGGAG

GTGCATAATGCCAAGACAAAGCCGCGGGAGGAGCAGTACAAC

AGCACGTACCGTGTGGTCAGCGTCCTCACCGTCCTGCACCAG

GACTGGCTGAATGGCAAGGAGTACAAGTGCAAGGTCTCCAAC

AAAGCCCTCCCAGCCCCCATCGAGAAAACCATCTCCAAAGCC

AAAGGGCAGCCCCGAGAACCACAGGTGTACACCCTGCCCCCA

TCCCGGGATGAGCTGACCAAGAACCAGGTCAGCCTGACCTGC

CTGGTCAAAGGCTTCTATCCCAGCGACATCGCCGTGGAGTGG

GAGAGCAATGGGCAGCCGGAGAACAACTACAAGACCACGCCT

CCCGTGCTGGACTCCGACGGCTCCTTCTTCCTCTACAGCAAG

CTCACCGTGGACAAGAGCAGGTGGCAGCAGGGGAACGTCTTC

-continued

TCATGCTCCGTGATGCATGAGGCTCTGCACAACCACTACACG

CAGAAGAGCCTCTCCCTGTCTCCGGGTAAATGA aflibercept codon-optimized #1
(CpG count = 57)

SEQ ID NO: 14

ATGGTTTCTTACTGGGATACCGGCGTGCTGCTGTGTGCCCTG

CTGTCTTGTCTGCTGCTGACCGGCTCTAGCAGCGGCTCTGAT

ACCGGCAGACCCTTCGTGGAAATGTACAGCGAGATCCCCGAG

ATCATCCACATGACCGAGGGCAGAGAGCTGGTCATCCCCTGC

AGAGTGACAAGCCCCAACATCACCGTGACTCTGAAGAAGTTC

CCTCTGGACACACTGATCCCCGACGGCAAGAGAATCATCTGG

GACAGCCGGAAGGGCTTCATCATCAGCAACGCCACCTACAAA

GAGATCGGCCTGCTGACCTGTGAAGCCACCGTGAATGGCCAC

CTGTACAAGACCAACTACCTGACACACAGACAGACCAACACC

ATCATCGACGTGGTGCTGAGCCCTAGCCACGGCATTGAACTG

TCTGTGGGCGAGAAGCTGGTGCTGAACTGTACCGCCAGAACC

GAGCTGAACGTGGGCATCGACTTCAACTGGGAGTACCCCAGC

AGCAAGCACCAGCACAAGAAACTGGTCAACCGGGACCTGAAA

ACCCAGAGCGGCAGCGAGATGAAGAAATTCCTGAGCACCCTG

ACCATCGACGGCGTGACCAGGTCTGACCAGGGCCTGTACACA

TGTGCCGCCAGCTCTGGCCTGATGACCAAGAAAAACAGCACC

TTCGTGCGGGTGCACGAGAAGGACAAGACCCACACCTGTCCT

CCATGTCCTGCTCCAGAACTGCTCGGCGGACCTTCCGTGTTC

CTGTTTCCTCCAAAGCCTAAGGACACCCTGATGATCAGCAGA

ACCCCTGAAGTGACCTGCGTGGTGGTGGATGTGTCCCACGAG

GATCCCGAAGTGAAGTTCAACTGGTACGTGGACGGCGTGGAA

GTGCACAACGCCAAGACCAAGCCTAGAGAGGAACAGTACAAT

AGCACCTACAGAGTGGTGTCCGTGCTGACCGTGCTGCACCAG

GATTGGCTGAACGGCAAAGAGTACAAGTGCAAGGTGTCCAAC

AAGGCCCTGCCTGCTCCTATCGAGAAAACCATCTCCAAGGCC

AAGGGCCAGCCCAGGGAACCCCAGGTTTACACACTGCCTCCA

AGCAGGGACGAGCTGACAAAGAACCAGGTGTCCCTGACCTGC

CTGGTCAAGGGCTTCTACCCTTCCGATATCGCCGTGGAATGG

GAGAGCAATGGCCAGCCTGAGAACAACTACAAGACAACCCCT

CCTGTGCTGGACAGCGACGGCTCATTCTTCCTGTACAGCAAG

CTGACAGTGGACAAGAGCAGATGGCAGCAGGGAAACGTGTTC

AGCTGCAGCGTGATGCACGAGGCCCTGCACAACCACTACACC

CAGAAGTCCCTGAGCCTGTCTCCTGGCAAGTGA aflibercept codon-optimized #2
(CpG count = 54)

SEQ ID NO: 15

ATGGTCAGCTATTGGGATACGGGCGTCCTCCTTTGTGCCCTT

CTGAGTTGTCTCTTGTTGACGGGAAGTAGTTCCGGAAGTGAC

ACTGGCCGACCATTTGTAGAAATGTACAGTGAGATCCCGGAA

ATCATCCACATGACCGAAGGCCGGGAGTTGGTTATACCATGC

CGGGTGACATCCCCGAACATTACCGTTACACTGAAGAAATTC

CCATTGGACACTTTGATACCTGATGGAAAGAGAATCATCTGG

GATTCCAGAAAAGGCTTTATTATCTCAAATGCTACATACAAA

GAAATCGGTCTTCTTACGTGTGAAGCAACCGTGAATGGTCAT

TTGTACAAGACTAACTACCTCACCCACAGGCAGACCAATACA

ATAATCGACGTCGTTCTCAGCCCCTCCCACGGAATTGAGCTT

AGTGTGGGGGAGAAATTGGTCTTGAATTGTACCGCCCGGACA

GAGTTGAATGTTGGCATTGACTTCAATTGGGAGTATCCATCT

AGTAAGCACCAACACAAAAAGCTTGTTAATCGGGACCTGAAG

ACTCAAAGCGGATCAGAAATGAAAAAGTTTCTCTCAACGTTG

ACAATAGACGGCGTGACGCGCTCTGATCAGGGTCTTTACACC

TGCGCTGCCAGCTCTGGGTTGATGACGAAAAAAAATTCTACA

TTTGTGCGGGTTCATGAAAAAGATAAGACACATACCTGTCCC

CCGTGTCCAGCGCCGGAATTGCTTGGGGGCCCCAGCGTATTC

CTTTTCCCCCCCAAGCCTAAAGACACGCTCATGATCTCTAGA

ACGCCGGAGGTCACCTGTGTGGTGGTGGACGTGTCTCATGAA

GATCCCGAGGTTAAATTCAATTGGTACGTAGATGGAGTCGAA

GTTCACAATGCAAAGACAAAGCCGAGAGAAGAGCAGTACAAT

AGCACCTACCGAGTTGTAAGTGTACTTACTGTCCTGCACCAA

GATTGGTTGAATGGAAAAGAGTATAAGTGTAAGGTCTCAAAT

AAGGCACTCCCAGCTCCCATAGAAAAAACGATATCTAAAGCG

AAGGGTCAGCCCAGAGAGCCTCAAGTGTACACGCTCCCTCCC

TCACGGGATGAGCTGACAAAAAACCAGGTTTCACTGACTTGT

TTGGTAAAGGGTTTTTATCCATCTGACATCGCTGTCGAGTGG

GAAAGCAATGGTCAACCGGAGAACAACTATAAGACAACCCCC

CCGGTTCTCGATTCAGATGGCTCCTTCTTCCTCTATTCTAAG

CTCACTGTTGATAAATCTCGGTGGCAACAAGGGAATGTTTTC

TCTTGCTCTGTTATGCACGAAGCATTGCATAATCATTATACA

CAAAAATCTCTTTCCCTTAGTCCAGGTAAATGA aflibercept codon-optimized #3
(CpG count = 0)

SEQ ID NO: 16

ATGGTGTCCTACTGGGACACAGGGGTGCTGCTGTGTGCCCTG

CTGTCTTGTCTGCTGCTGACTGGCTCTAGCTCTGGCTCTGAC

ACAGGCAGACCCTTTGTGGAAATGTACTCTGAGATCCCTGAG

ATCATCCACATGACAGAGGGCAGAGAGCTGGTCATCCCCTGC

AGAGTGACAAGCCCCAACATCACAGTGACCCTGAAGAAGTTC

CCTCTGGACACACTGATCCCTGATGGCAAGAGAATCATCTGG

GACAGCAGAAAGGGCTTCATCATCAGCAATGCCACCTACAAA

GAGATTGGCCTGCTGACCTGTGAAGCCACAGTGAATGGCCAC

CTGTACAAGACCAACTACCTGACACACAGACAGACCAACACC

-continued

ATCATTGATGTGGTGCTGAGCCCCAGCCATGGCATTGAGCTG
TCTGTGGGAGAGAAGCTGGTGCTGAACTGCACAGCCAGAACA
GAGCTGAATGTGGGCATTGACTTCAACTGGGAGTACCCCAGC
AGCAAGCACCAGCACAAGAAACTGGTCAACAGGGACCTGAAA
ACCCAGAGTGGCTCTGAGATGAAGAAATTCCTGAGCACCCTG
ACCATTGATGGGGTCACCAGATCTGACCAGGGCCTGTACACA
TGTGCTGCCAGCTCTGGACTGATGACCAAGAAAAACAGCACC
TTTGTCAGAGTGCATGAGAAGGACAAGACCCACACCTGTCCT
CCATGTCCTGCACCTGAGCTGCTTGGAGGCCCCTCTGTGTTC
CTGTTTCCTCCAAAGCCTAAGGACACCCTGATGATCAGCAGA
ACACCTGAAGTGACCTGTGTGGTGGTGGATGTGTCCCATGAG
GACCCAGAAGTGAAGTTCAATTGGTATGTGGATGGGGTTGAA
GTGCACAATGCCAAGACCAAGCCTAGAGAGGAACAGTACAAC
TCCACCTACAGAGTGGTGTCAGTGCTGACAGTGCTGCACCAG
GACTGGCTGAATGGCAAAGAGTACAAGTGCAAGGTGTCCAAC
AAGGCCCTGCCTGCTCCTATTGAGAAAACCATCTCCAAGGCC
AAGGGCCAGCCTAGGGAACCCCAGGTTTACACACTGCCACCT
AGCAGGGATGAGCTGACAAAGAACCAGGTGTCCCTGACCTGC
CTGGTCAAGGGCTTCTACCCCTCTGACATTGCTGTGGAATGG
GAGAGCAATGGCCAGCCTGAGAACAACTACAAGACAACCCCT
CCTGTGCTGGACTCTGATGGCTCATTCTTCCTGTACAGCAAG
CTGACTGTGGACAAGAGCAGATGGCAGCAGGGAAATGTGTTC
AGCTGCTCTGTGATGCATGAGGCCCTGCACAACCACTACACC
CAGAAAAGCCTGAGCCTGTCTCCTGGCAAGTGA aflibercept codon-optimized #4
(CpG count = 56)

SEQ ID NO: 17

ATGGTTTCTTACTGGGATACCGGCGTGCTGCTGTGTGCCCTG
CTGTCTTGTCTGCTGCTGACCGGCTCTAGCAGCGGCTCTGAT
ACCGGCAGACCCTTCGTGGAAATGTACAGCGAGATCCCCGAG
ATCATCCACATGACCGAGGGCAGAGAGCTGGTCATCCCCTGC
AGAGTGACAAGCCCCAACATCACCGTGACTCTGAAGAAGTTC
CCTCTGGACACACTGATCCCCGACGGCAAGAGAATCATCTGG
GACAGCCGGAAGGGCTTCATCATCAGCAACGCCACCTACAAA
GAGATCGGCCTGCTGACCTGTGAAGCCACCGTGAATGGCCAC
CTGTACAAGACCAACTACCTGACACACAGACAGACCAACACC
ATCATCGACGTGGTGCTGAGCCCTAGCCACGGCATTGAACTG
TCTGTGGGCGAGAAGCTGGTGCTGAACTGTACCGCCAGAACC
GAGCTGAACGTGGGCATCGACTTCAACTGGGAGTACCCCAGC
AGCAAGCACCAGCACAAGAAACTGGTCAACCGGGACCTGAAA
ACCCAGAGCGGCAGCGAGATGAAGAAATTCCTGAGCACCCTG
ACCATCGACGGCGTGACCAGGTCTGACCAGGGCCTGTACACA

-continued

TGTGCCGCCAGCTCTGGCCTGATGACCAAGAAAAACAGCACC
TTCGTGCGGGTGCACGAGAAGGACAAGACCCACACCTGTCCT
CCATGTCCTGCTCCAGAACTGCTCGGCGGACCTTCCGTGTTC
CTGTTTCCTCCAAAGCCTAAGGACACCCTGATGATCAGCAGA
ACCCCTGAAGTGACCTGCGTGGTGGTGGATGTGTCCCACGAG
GATCCCGAAGTGAAGTTCAACTGGTACGTGGACGGCGTGGAA
GTGCACAACGCCAAGACCAAGCCTAGAGAGGAACAGTACAAT
AGCACCTACAGAGTGGTGTCCGTGCTGACCGTGCTGCACCAG
GATTGGCTGAACGGCAAAGAGTACAAGTGCAAGGTGTCCAAC
AAGGCCCTGCCTGCTCCTATCGAGAAAACCATCTCCAAGGCC
AAGGGCCAGCCCAGGGAACCCCAGGTTTACACACTGCCTCCA
AGCAGGGACGAGCTGACAAAGAACCAGGTGTCCCTGACCTGC
CTGGTCAAGGGCTTCTACCCTTCCGATATCGCCGTGGAATGG
GAGAGCAATGGCCAGCCTGAGAACAACTACAAGACAACCCCT
CCTGTGCTGGACAGCGACGGCTCATTCTTCCTGTACAGCAAG
CTGACAGTGGACAAGAGCAGATGGCAGCAGGGAAACGTGTTC
AGCTGCAGCGTGATGCACGAGGCCCTGCACAACCACTACACC
CAGAAGTCCCTGAGCCTGTCTCCTGGCAAGTGA aflibercept codon-optimized #5
(CpG count =56)

SEQ ID NO: 18

ATGGTGTCCTACTGGGATACAGGCGTGCTGCTGTGTGCCCTG
CTGTCTTGTCTGCTGCTGACCGGCTCTAGCAGCGGCTCTGAT
ACCGGCAGACCCTTCGTGGAAATGTACAGCGAGATCCCCGAG
ATCATCCACATGACCGAGGGCAGAGAGCTGGTCATCCCCTGC
AGAGTGACAAGCCCCAACATCACCGTGACTCTGAAGAAGTTC
CCTCTGGACACACTGATCCCCGACGGCAAGAGAATCATCTGG
GACAGCCGGAAGGGCTTCATCATCAGCAACGCCACCTACAAA
GAGATCGGCCTGCTGACCTGTGAAGCCACCGTGAATGGCCAC
CTGTACAAGACCAACTACCTGACACACAGACAGACCAACACC
ATCATCGACGTGGTGCTGAGCCCTAGCCACGGCATTGAACTG
TCTGTGGGCGAGAAGCTGGTGCTGAACTGTACCGCCAGAACC
GAGCTGAACGTGGGCATCGACTTCAACTGGGAGTACCCCAGC
AGCAAGCACCAGCACAAGAAACTGGTCAACCGGGACCTGAAA
ACCCAGAGCGGCAGCGAGATGAAGAAATTCCTGAGCACCCTG
ACCATCGACGGCGTGACCAGATCTGACCAGGGCCTGTACACA
TGTGCCGCCAGCTCTGGCCTGATGACCAAGAAAAACAGCACC
TTCGTGCGGGTGCACGAGAAGGACAAGACCCACACCTGTCCT
CCATGTCCTGCTCCAGAACTGCTCGGCGGACCTTCCGTGTTC
CTGTTTCCTCCAAAGCCTAAGGACACCCTGATGATCAGCAGA
ACCCCTGAAGTGACCTGCGTGGTGGTGGATGTGTCCCACGAG
GATCCCGAAGTGAAGTTCAATTGGTACGTGGACGGCGTGGAA

-continued

GTGCACAACGCCAAGACCAAGCCTAGAGAGGAACAGTACAAT

AGCACCTACAGAGTGGTGTCCGTGCTGACCGTGCTGCACCAG

GATTGGCTGAACGGCAAAGAGTACAAGTGCAAGGTGTCCAAC

AAGGCCCTGCCTGCTCCTATCGAGAAAACCATCTCCAAGGCC

AAGGGCCAGCCTAGGGAACCCCAGGTTTACACACTGCCTCCA

AGCAGGGACGAGCTGACAAAGAACCAGGTGTCCCTGACCTGC

-continued

CTGGTCAAGGGCTTCTACCCTTCCGATATCGCCGTGGAATGG

GAGAGCAATGGCCAGCCTGAGAACAACTACAAGACAACCCCT

CCTGTGCTGGACAGCGACGGCTCATTCTTCCTGTACAGCAAG

CTGACAGTGGACAAGAGCAGATGGCAGCAGGGAAACGTGTTC

AGCTGCAGCGTGATGCACGAGGCCCTGCACAACCACTACACC

CAGAAGTCCCTGAGCCTGTCTCCTGGCAAGTGA

What is claimed is:

1. A composition comprising:

(i) a first polynucleotide comprising a first sequence operably linked to a first promoter and a second sequence operably linked to a second promoter, wherein the first sequence encodes an adeno-associated virus (AAV) capsid protein, and wherein the second sequence encodes an AAV rep protein; and (ii) a second polynucleotide comprising a third sequence operably linked to a CAG promoter and a β-globin poly(A), wherein the third sequence comprises a codon-optimized nucleic acid sequence encoding a Vascular Endothelial Growth Factor (VEGF) inhibitor, wherein the third sequence comprises the sequence of SEQ ID NO: 14, SEQ ID NO: 15, SEQ ID NO: 16, or SEQ ID NO: 18; and wherein the codon-optimized nucleic acid sequence encoding a VEGF inhibitor comprises the amino acid sequence of SEQ ID NO: 1.

2. The composition of claim 1, wherein the first promoter or the second promoter is a p10 promoter or a polh promoter.

3. The composition of claim 1, wherein the second polynucleotide comprises:

a) an intron comprising a chimeric intron or a regulatory element comprising a tripartite leader sequence from adenovirus (TPL) and an enhancer element from the adenovirus major late promoter (eMLP) sequence; or b) a Kozak sequence.

4. A recombinant adeno-associated virus (rAAV) particle prepared by transfecting the composition of claim 1 into cells, wherein the cells are Sf9 cells, or HEK293 cells or derivative thereof and wherein the rAAV comprises the second polynucleotide.

5. A method for treating an ocular disease in a subject in need thereof, comprising administering a therapeutically effective amount of the composition of claim 1 to the subject, wherein the ocular disease is selected from the group consisting of wet age-related macular degeneration (wet AMD), diabetic retinopathy, diabetic macular edema, proliferative diabetic retinopathy, and macular edema.

6. A polynucleotide, comprising a codon-optimized nucleic acid sequence encoding a Vascular Endothelial Growth Factor (VEGF) inhibitor comprising the amino acid sequence of SEQ ID NO: 1, and wherein the codon-optimized nucleic acid sequence comprises SEQ ID NO: 14, SEQ ID NO: 15, SEQ ID NO: 16, or SEQ ID NO: 18.

7. The polynucleotide of claim 6, further comprising a promoter, wherein the promoter is a CMV promoter, CAG promoter, MNDU3 promoter, PGK promoter, EF1a promoter, or an eye specific promoter, and wherein the eye-specific promoter is selected from the group consisting of RPE 65 gene promoter, human retinal binding protein gene promoter, murine 11-cis retinoid alcohol dehydrogenase gene promoter, rhodopsin promoter, rhodoposin kinase promoter, tissue inhibitor of metalloproteinase 3 promoter, photoreceptor retinol binding protein promoter, vitelliform macular dystrophy 2 promoter, and interphotoreceptor retinoid-binding protein promoter.

8. The polynucleotide of claim 6, further comprising:

(i) a poly(A) sequence, wherein the poly(A) sequence is hGH poly(A), SV40 poly(A), or β-globin poly(A); or (ii) an intron comprising a chimeric intron or a regulatory element comprising a tripartite leader sequence from adenovirus (TPL) and an enhancer element from the adenovirus major late promoter (eMLP) sequence; or (iii) a Kozak sequence.

9. A recombinant adeno-associated virus (rAAV) particle, comprising the polynucleotide of claim 6.

10. A method for treating an ocular disease in a subject in need thereof, comprising administering a therapeutically effective amount of the rAAV particle of claim 9 to the subject, wherein the ocular disease is selected from the group consisting of wet age-related macular degeneration (wet AMD), diabetic retinopathy, diabetic macular edema, proliferative diabetic retinopathy, and macular edema.

11. A composition comprising:

(i) a first polynucleotide comprising a first sequence operably linked to a first promoter and a second sequence operably linked to a second promoter, wherein the first sequence encodes an adeno-associated virus (AAV) capsid protein, and wherein the second sequence encodes an AAV rep protein; and (ii) a second polynucleotide comprising a third sequence operably linked to a CAG promoter and a β-globin poly(A), wherein the third sequence comprises a codon-optimized nucleic acid sequence encoding a Vascular Endothelial Growth Factor (VEGF) inhibitor, wherein the third sequence consists of the sequence of SEQ ID NO: 14; and wherein the codon-optimized nucleic acid sequence encoding a VEGF inhibitor consists of the amino acid sequence of SEQ ID NO: 1.

* * * * *